US009266844B2

(12) United States Patent
Sarafianos et al.

(10) Patent No.: US 9,266,844 B2
(45) Date of Patent: Feb. 23, 2016

(54) SUPPRESSION OF SARS REPLICATION BY SARS HELICASE INHIBITORS

(71) Applicant: The Curators of the University of Missouri, Columbia, MO (US)

(72) Inventors: Stefan G. Sarafianos, Columbia, MO (US); Adeyemi O. Adedeji, Columbia, MO (US); Kamlendra Singh, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 13/919,951

(22) Filed: Jun. 17, 2013

(65) Prior Publication Data

US 2014/0005241 A1  Jan. 2, 2014

Related U.S. Application Data

(60) Provisional application No. 61/689,952, filed on Jun. 15, 2012.

(51) Int. Cl.
*A61K 31/4196* (2006.01)
*C12Q 1/18* (2006.01)
*C07D 249/12* (2006.01)

(52) U.S. Cl.
CPC .......... *C07D 249/12* (2013.01); *A61K 31/4196* (2013.01); *C12Q 1/18* (2013.01); *G01N 2333/165* (2013.01)

(58) Field of Classification Search
None
See application file for complete search history.

(56) References Cited

PUBLICATIONS

Talawar et al., Indian Journal of Heterocyclic Chemistry, vol. 5, Jan.-Mar. 1996, pp. 215-218.*
CAS RN 675104-49-1, Indexed in STN Registry database, Entered STN Apr. 14, 2004. Accessed Jun. 15, 2015.*
Ito et al. In Cancer Science 94(1), 3-8 (2003).*
Adedeji et al., "Identification of a Novel Inhibitor That Prevents SARS-CoV Replication by Interfering with the Unwinding Mechanism of the Viral Helicase," *12th Annual Symposium on Antiviral Drug Resistance*, Nov. 2011.
Adedeji et al., "Severe Acute Respiratory Syndrome Coronavirus Replication Inhibitor That Interferes with the Nucleic Acid Unwinding of the Viral Helicase," *Antimicrobial Agents and Chemotherapy* 56(9):4718-4728, Sep. 2012.
Adedeji et al., "Mechanism of nucleic acid unwinding by SARS-CoV Helicase," *PLoS One* 7(5):e36521, May 2012.
Adedeji et al., "SARS-CoV Replication Inhibitor that Interferes with the Nucleic Acid Unwinding of the Viral Helicase," *Antimicrob Agents Chemother* 56:4718-28, 2012.
Adedeji et al., "Structural and biochemical basis for the difference in the helicase activity of two different constructs of sars-cov helicase," *Cell Mol Biol* 58:114-121, 2012.
Alasdair et al., "Q-SiteFinder: an energy-based method for the prediction of protein-ligand binding sites," *Oxford Journals* 21:1906-1908, 2005.
Almazan et al., "Construction of a severe acute respiratory syndrome coronavirus infections cDNA clone and a replicon to study coronavirus RNA synthesis," *J Virol* 80:10900-10906, 2006.
Durk et al., "Inhibitors of foot and mouth disease virus targeting a novel pocket of the RNA-dependent RNA polymerase," *PLoS One* 5:e15049, 2010.
International Search Report and Written Opinion issued in PCT/US2013/0461999, dated Nov. 5, 2013.
Ivanov et al., "Multiple enzymatic activities associated with severe acute respiratory syndrome coronavirus helicase," *J Virol* 78:5619-5632, 2004.
Kleymann, "New antiviral drugs that target herpesvirus helicase primase enzymes," *Herpes* 10(2):46-52, 2003.
Kwong et al., "Viral and Cellular RNA Helicases as Antiviral Targets," *Nature Reviews Drug Discovery* 4:845-853, Oct. 2005.
Sarafianos et al., "Mechanism of polyoxometalate-mediated inactivation of DNA polymerases: an analysis with HIV-1 reverse transcriptase indicates specificity for the DNA-binding cleft," *Biochem J* 319(Pt 2):619-626, 1996.
Sharma et al., "DNA helicases as targets for anti-cancer drugs," *Curr Med Chem Anticancer Agents* 5(3):183-99, 2005.
Tanner et al., "The severe acute respiratory syndrome (SARS) coronavirus NTPase/helicase belongs to a distinct class of 5' to 3' viral helicases," *J Biol Chem* 278:39578-39582, 2003.
Zhang et al., "A simple statistical parameter for use in evaluation and validation of high throughput screening assays," *J Biomol Screen* 4:67-73, 1999.

* cited by examiner

*Primary Examiner* — Alicia L Otton
(74) *Attorney, Agent, or Firm* — Dentons US LLP

(57) ABSTRACT

The present invention relates to compounds, compositions, and methods, for treating subjects suspected of needing treatment for a Nidovirales virus infection. In certain embodiments, the compounds comprise Nidovirales helicase inhibitors that do not significantly affect helicase ATPase enzymatic activity or nucleic acid binding activity of the helicase.

17 Claims, 13 Drawing Sheets

SUPPRESSION OF SARS REPLICATION BY SARS HELICASE INHIBITORS

CROSS REFERENCE TO RELATED APPLICATIONS

Figure 1:
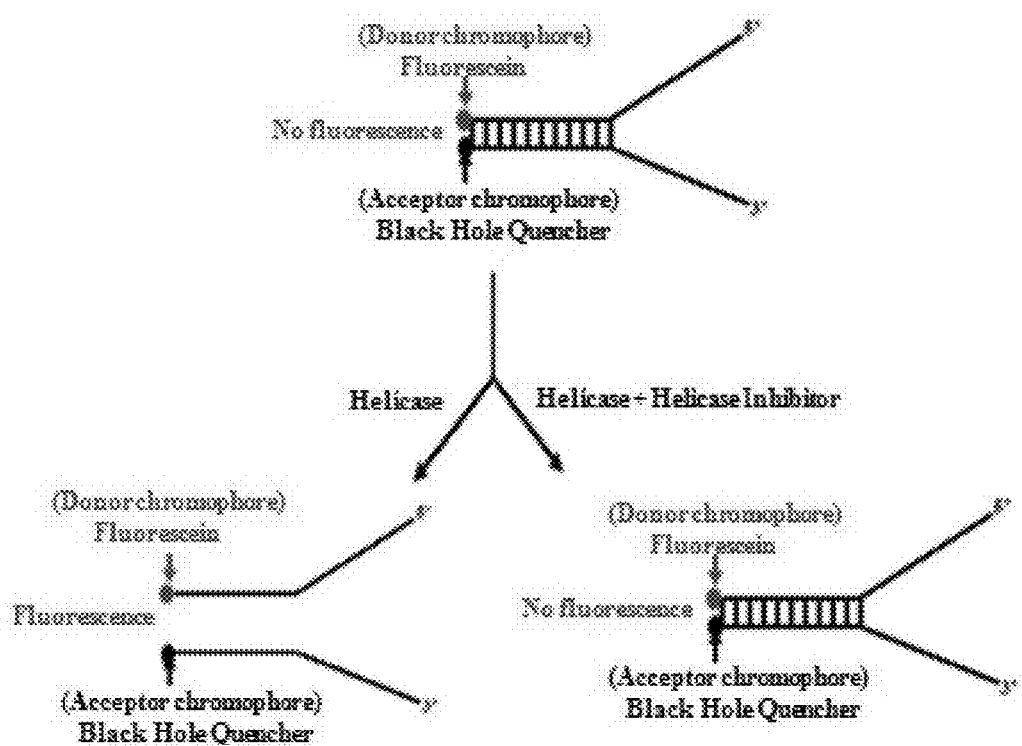

This application claims the benefit of U.S. Provisional Application No. 61/689,952, filed on Jun. 15, 2012, herein incorporated by reference in its entirety.

STATEMENT OF GOVERNMENT SUPPORT

This invention was made with Government support under the Grants No. AI076119, AI94715, AI079801, and AI074389 awarded by the National Institutes of Health. The Government has certain rights in the invention.

INCORPORATION OF SEQUENCE LISTING

The sequence listing that is contained in the file named "UVMO108US_ST25.txt", which is 3.43 kilobytes as measured in Microsoft Windows operating system and was created on Jun. 17, 2013, is filed electronically herewith and incorporated herein by reference.

BACKGROUND OF INVENTION

1. Field of the Invention

The present invention relates to antiviral compounds for the treatment of SARS-CoV infections, more specifically, to a new class of small molecule inhibitors of SARS-CoV replication that block the helicase activity of nsp13.

2. Background of the Invention

Severe acute respiratory syndrome (SARS) is a highly contagious disease caused by SARS-associated coronavirus (SARS-CoV) for which there are no approved treatments. SARS causes a life-threatening viral respiratory illness, which emerged from Southern China and spread to other parts of the world including North America, South America, and Europe. There is currently no approved therapeutic agent for the treatment of SARS infections. Although, SARS currently does not pose a public threat, the likelihood of future occurrences of both SARS-CoV and related viruses necessitates continuous research for identification of antiviral therapies.

SUMMARY OF INVENTION

In one aspect, the invention provides methods for treating a subject suspected of needing treatment for a Nidovirales virus infection, comprising administering an effective amount of a compound of formula II:

a derivative, or a pharmaceutically acceptable salt thereof; wherein the effective amount is capable of inhibiting a Nidovirales virus helicase; wherein B represents Sulfur or Oxygen; wherein X, Y, and Z are independently selected from one another from the group consisting of H, —SH, and —O—R; wherein R is selected from the group consisting of H, alkyl, alkenyl, alkynyl, C3-C6 cyclo-alkyl, cyclo-alkyl-alkyl, aryl, hetero-aryl, aryl-alkyl, heteroaryl-alkyl, heterocyclyl, heterocycly-lalkyl, lkylsulfonyl, and arylsulfonyl. In one embodiment, the one or more R groups are substituted by one, two, or three substituents selected from the group consisting of: halogens, azido (—N3), cyano (—CN), hydroxyl (—OH), nitro (—NO2), alkyl, aryl, arylalkyl, —O-alkyl, and —O-aryl. In another embodiment, halogen is selected from the group consisting of —F, —Cl, —Br, and —I. In yet another embodiment, the compound is a compound of formula I:

a derivative, or a pharmaceutically acceptable salt thereof, wherein the effective amount is capable of inhibiting a Nidovirales virus helicase.

In a method of the invention, Nidovirales virus infection may be Severe Acute Respiratory Syndrome (SARS). The Nidovirales virus may also comprise a SARS-associated coronavirus (SARS-CoV). In one embodiment, the Nidovirales virus comprises a Coronaviridae virus. The Nidovirales virus may comprises a MERS-CoV and may comprise HCoV-229E and/or NL63. In certain embodiments, the effective amount is determined according to standard practices well known in the art. In a method of the invention, administering a compound of the invention may potentially comprise any method, such as an oral route, non-oral route, parenterally, intravenously, subcutaneously, and intraperitoneally. In one embodiment, the administering is transdermally, sublingually, and buccally. In specific embodiments of the invention, a subject is defined as a mammal, animal or human. In one embodiment, a method of the invention further comprises identifying the subject as needing treatment for a Nidovirales virus infection. In certain embodiments, the subject is suspected of having been exposed to a Nidovirales virus infection or needing prophylactic treatment.

In another aspect, the invention provides a pharmaceutical composition comprising a compound of the invention, such as formula II or a derivative, or a pharmaceutically acceptable salt thereof as described herein. The compound of the invention in one embodiment is Formula I, or a salt thereof, and one or more pharmaceutically-acceptable excipients.

In yet another aspect, the invention provides a method of inhibiting replication of a Nidovirales virus comprising the step of contacting a sample containing the Nidovirales virus with a compound of the invention.

In still yet another aspect, the invention provides a method of inhibiting replication of a Nidovirales virus or treating a subject suspected of needing treatment for a Nidovirales virus infection comprising contacting a sample containing the Nidovirales virus or providing the subject suspected of needing treatment with a compound capable of inhibiting unwinding activity of a Nidovirales helicase, wherein the compound does not affect ATPase enzymatic activity or nucleic acid binding activity of the helicase. In certain embodiments, the compound is formula II or a derivative, or a pharmaceutically acceptable salt thereof as described herein. In another embodiment, the compound is formula I, derivatives of formula I, or salts thereof. The helicase may be nsp13.

Figures 8A, 8B:
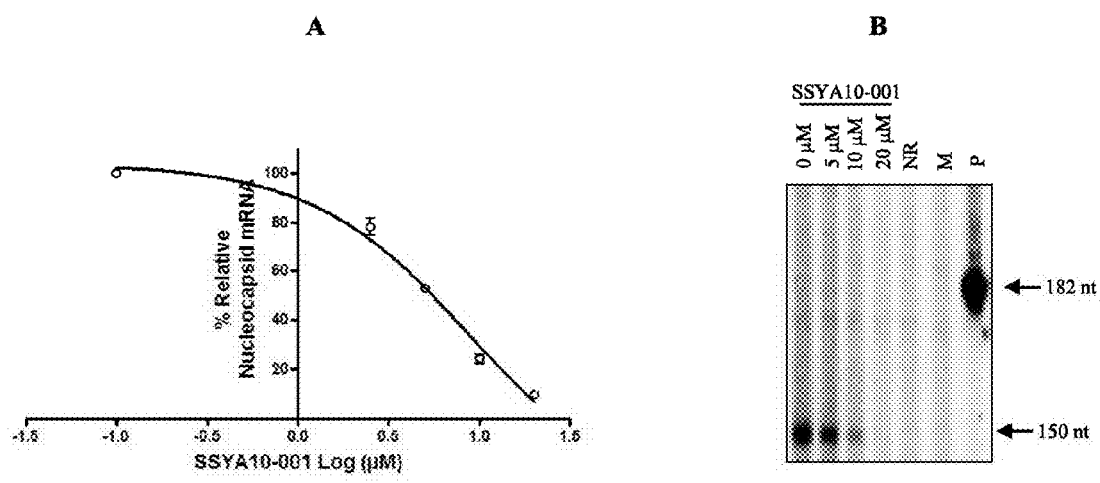

In still yet another aspect, the invention provides a method of identifying an antiviral compound capable of inhibiting a Nidovirales virus replication, comprising: incubating a helicase of the Nidovirales virus with a substrate of the helicase in the presence of one or more candidate compounds; detecting helicase activity; relating helicase activity to one or more members of the plurality of candidate compounds; identifying one or more candidate compounds capable of inhibiting helicase unwinding activity; testing whether the one or more candidate compounds capable of inhibiting helicase activity affect ATPase enzymatic activity or nucleic acid binding activity of the helicase; identifying the antiviral compound against a Nidovirales virus, which is capable of inhibiting helicase unwinding activity without reducing ATPase enzymatic activity or nucleic acid binding activity.

In still yet another aspect, the invention provides a method of optimizing a lead compound, comprising: generating one or more chemical derivatives of the compound of formula I: testing the one or more derivatives for helicase unwinding-inhibitory activity, identifying one or more optimized lead compounds having an improved helicase-inhibitory-activity. Still further provided by the invention is a method of optimizing a lead compound, comprising: generating one or more chemical derivatives of the compound of formula I: testing the one or more derivatives for Nidovirales virus replication suppression activity, identifying one or more optimized lead compounds having an Nidovirales virus replication suppression activity.

BRIEF DESCRIPTION OF THE DRAWINGS

FIG. 1. Schematic representation of the fluorescence helicase assay. A dsDNA substrate (forked substrate) was designed with 2 chromophores at the ends of the complementary strands (i.e. fluorescein and black hole quencher-dsDNA). In the presence of an active helicase, the two complementary strands are separated allowing fluorescence detection from the fluorescein chromophore, whose excitation occurs at 495 nm and emission at 520 nm. In the presence of a potential helicase inhibitor, the two complementary strands will not be separated; therefore, fluorescence will not be detected.

FIGS. 2A and 2B. Validation of nsp13 inhibition using a gel-based helicase assay. FIG. 2A) 50 nM nsp13 was incubated in the presence of 20 μM of the compound of formula I (SSYA10-001), 20 mM HEPES, 20 mM NaCl, 0.01% BSA, 2 mM DTT, 5% glycerol, and 5 mM MgCl2. The helicase reaction was initiated by the addition of 100 nM 31/18-mer (13ss:18ds) as substrate at 30° C. (Cy3-labeled), 0.5 mM ATP and 2 μM unlabeled ssDNA with sequence complementary to the unlabeled DNA strand. The reactions were allowed to proceed for 10 min at 30° C. and the reaction was quenched with 100 mM EDTA, 0.2% SDS, and 20% glycerol. The products were separated and analyzed by 6% non-denaturing PAGE. FIG. 2 B) $IC_{50}$ of SSYA10-001 was determined using the gel-based assay as described in FIG. 2A with varying concentrations of the compound (0, 2.5, 10, 20, 40, 80 μM). Reaction products were resolved and quantitated using the ImageQuant software (Pharmacia). The fraction of unwound DNA (○), RNA (■) and SARS-CoV specific RNA (♦) was plotted against the concentration of the inhibitor and the data were fit to dose response curves using the GraphPad Prism 5.0 (GraphPad Inc.) to determine the $IC_{50}$ (mean±SD) of 5.7±2.3 μM with RNA 31/18-mer (13ss:18ds), 5.6±0.5 μM with SARS-CoV specific RNA 31/18-mer (13ss:18ds), and 5.3±2.0 μM with the DNA substrates 31/18-mer (13ss:18ds). Experiments were performed three times; ± and error bars represent standard deviation from three independent experiments.

FIG. 3. Chemical structures, name, and $IC_{50}$ of an identified nsp13 inhibitor.

FIGS. 4A and 4B. Effect of SSYA10-001 on other helicases and polymerases activity. FIG. 4A) The plot for the fractions of unwound RNA for the HCV NS3h helicase (◇), Dengue virus NS3 helicase (○) and SARS-CoV nsp13 helicase (■). Experiments were performed three times, and error bars represent standard deviation from three independent experiments. FIG. 4B) The plot for the fractions of the polymerization product for the KF (◇), MoMLV-RT (○), and FMDV 3Dpol (■). Experiments were performed three times, and error bars represent standard deviation from three independent experiments.

FIGS. 5A and 5B. Non-competitive inhibition of nsp13 by SSYA10-001 under steady state conditions. Kinetic experiments with nsp13 were conducted in 96-well plates using Fluorescence-based assay in the presence of increasing concentrations of SSYA10-001 (0 to 20 μM), varying either the ATP substrate (0.0125 mM-7.5 mM) (FIG. 5A) or the forked substrate (0.01 μM to 1 μM) (FIG. 5B). In both cases the X-axis intercepts (−1/Km for the ATP or forked substrates) are not affected by the inhibitor concentrations, which is the feature of non-competitive inhibition.

FIGS. 6A and 6B. Investigation of the effect of SSYA10-001 on the nucleic acid binding and ATP hydrolysis of nsp13. FIG. 6A) 25 nM nsp13 was pre-incubated with varying concentrations of SSYA10-001 (0, 2.5, 10, 20, 40 μM) followed by incubation with 5 nM Cy3-labeled version of the forked substrate in 20 mM HEPES (pH 7.5), 20 mM NaCl, 5 mM MgCl2, 1 mM DTT, 0.1 mg/ml BSA and 5% glycerol at 30° C. for 20 minutes. The reaction samples were then analyzed on a non-denaturing 6% polyacrylamide gel. FIG. 6B) 50 nM pre-incubated nsp13 and varying concentrations of SSYA10-001 (0, 2.5, 10, 20, 40 μM) were mixed with 5 μM gamma-$^{32}P$-ATP for 10 sec. The reaction products were separated by thin-layer chromatography and visualized by autoradiography.

FIGS. 7A, 7B, 7C, and 7D. Determination of nucleic acid binding of SSYA10-001. FIG. 7A) A schematic depiction of Klenow Fragment (KF) strand displacement and polymerization assay design shows a DNA substrate with a 3' end primer that is annealed with a complementary strand at the 5' end. Primer extension can only take place in the presence of a polymerase with strand displacement activity such as KF. The presence of a dsDNA chelator such as pico green prevents strand displacement and therefore prevents primer extension. FIGS. 7B and 6C) Varying concentrations of SSYA10-001 (0, 5, 10, 20 μM) (FIG. 7B) and pico green (1×, 2×, 3×) (FIG. 7C) were pre-incubated with 20 nM 13ds:4ss:18ds DNA substrate in 50 mM Tris-HCl pH 7.5, 50 mM NaCl, 5 mM MgCl2, 1 mM DTT, 5% glycerol and 50 μM dNTPs. The reaction was initiated by the addition of 20 nM KF at 37° C. for 10 min and the reactions were resolved and analyzed on a 15% polyacrylamide 7 m urea gel. FIG. 7D) Varying concentrations of the SSYA10-001 (0, 2.5, 5, 10, 20 and 40 μM) were preincubated with dsDNA (31/18-mer) for 10 minutes followed by addition of 1× final concentration of pico green reagent, and immediate fluorescence measurement. The percent relative fluorescence was plotted against the concentration of the inhibitor and the data were fit to dose response curves using the GraphPad Prism 5.0 (GraphPad Inc.). Experiments were performed in triplicates in two independent experiments.

FIGS. 8A and 8B. Measurement of SARS-CoV replication in the presence of SSYA10-001. FIG. 8A) HEK 293T cells were transfected with mock or the SARS CoV replicon or a non-replicative construct by using Lipofectamine 2000 (Invitrogen) in the presence of varying concentrations of SSYA10-001 (0, 2.5, 5, 10, and 20 μM). Total RNA was isolated at 48 hours post transfection and analyzed by RT-qPCR with specific oligonucleotides to detect N gene mRNA. Triplicate RT-qPCR products were amplified in parallel. Average N mRNA quantities for each concentration was normalized internally using the cycle threshold (CT) of the housekeeping gene U6. Samples were additionally normalized to the NRC controls and the RQ value for each sample was obtained using the relative quantity method ($2-\Delta\Delta CT$). The RQ value for each sample was then normalized to the RQ value of the NRC (which is 1), and the data were graphed as percent relative replicon activity against the log of the inhibitor concentrations in μM using the dose response curve in GraphPad prism 5.0 (GraphPad Inc). Experiments were repeated three times and error bars represent standard deviation between triplicate samples. FIG. 8B) HEK 293T cells were transfected with mock or the SARS CoV replicon or a non-replicative construct by using Lipofectamine 2000 (Invitrogen) in the presence of varying concentrations of SSYA10-001 (0, 5, 10, and 20 μM). Total RNA was isolated at 48 hours post transfection. RNAse protection assay was performed by overnight annealing of the newly generated probes with the total intracellular RNA followed by RNase A and T1 treatment of the annealed reaction. The reaction samples were analyzed on a 6% Urea-PAGE and visualized using the phosphorimager (FLA 5000, FujiFilm). The Lane P represents the probe by itself, M represents mock transfection lane, NR depicts sample from the non-replicative construct and nt represents nucleotides. The probe was 182 nt long because of the extra 32 nt between Sp6 transcription start site and XbaI site of the pGEM-3Z vector.

Figure 9:
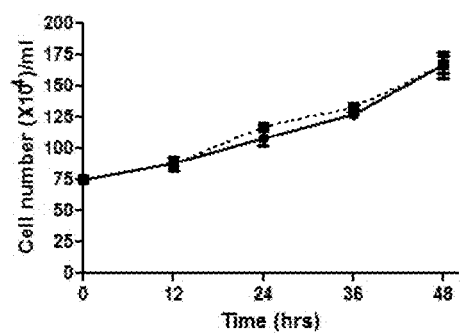

FIG. 9. Cytostatic effect of SSYA10-001. HEK 293T cells (7.5×105) were treated with 250 μM SSYA10-001. The medium was changed and fresh compound was added daily. Viability of the cells was assessed every 12 h, up to 48 h, by trypan blue exclusion. The number of viable cells counted was plotted against time using the Graphpad Prism 5.0 (GraphPad Inc.). Experiments were performed in triplicate and error bars represent standard deviation between triplicate samples. ● represents 250 μM SSYA10-001 and ■ represents 0.2% DMSO as control.

Figure 10:
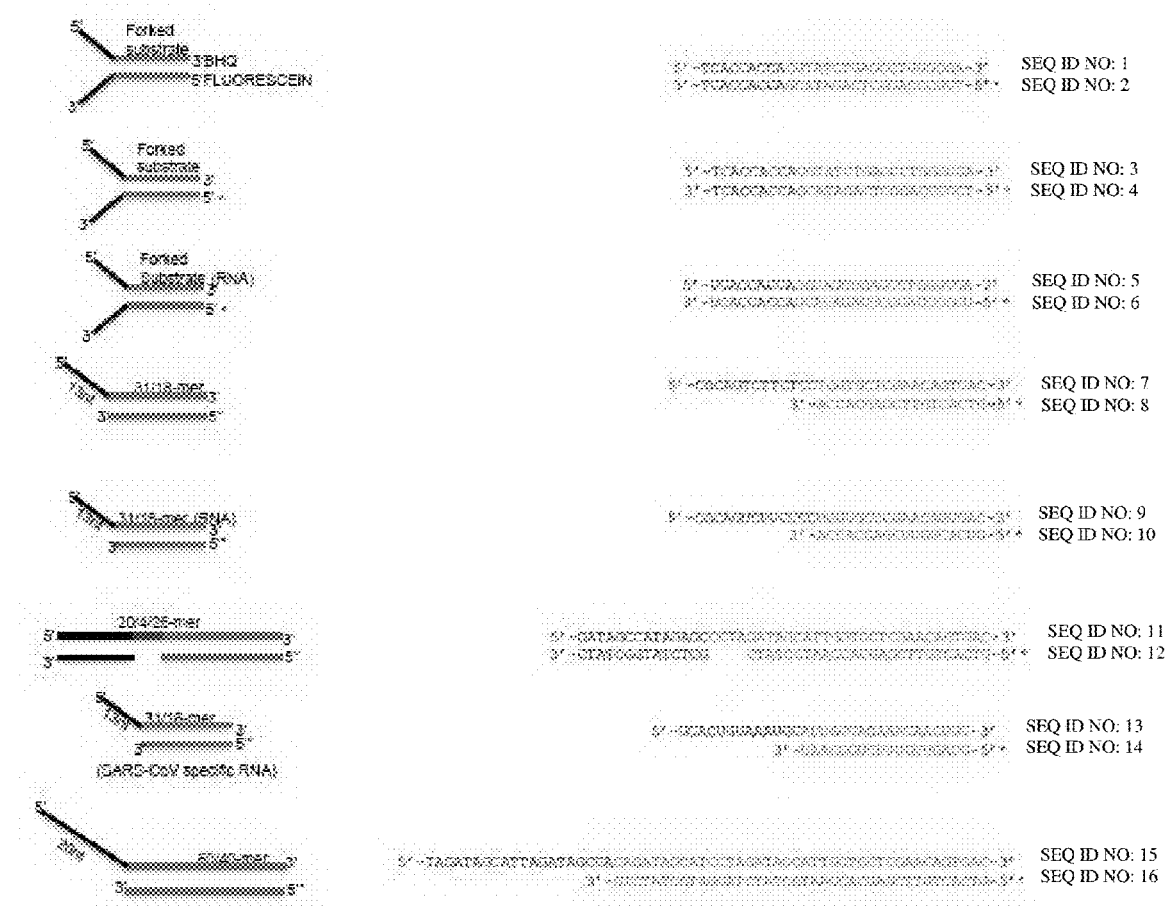

FIG. 10. Oligonucleotides and substrates used in this study. The Cy3-labeled strands are marked by asterisks; the sequences in green denote complementary sequences while the sequences in black denote non-complementary sequences. Oligonucleotides were the following:

```
                                       (SEQ ID NO: 1)
5'-TCACCACCACGTATCTGAGCCTGGGCGA-3;

(SEQ ID NO: 2)
3'-TCACCACCAGCATAGACTCGGACCCGCT-5;

(SEQ ID NO: 3)
5'-TCACCACCACGTATCTGAGCCTGGGCGA-3';

(SEQ ID NO: 4)
3'-TCACCACCAGCATAGACTCGGACCCGCT-5';

(SEQ ID NO: 5)
5'-UCACCACCACGUAUCUGAGCCUGGGCGA-3';

(SEQ ID NO: 6)
3'-UCACCACCAGCAUAGACUCGGACCCGCU-5';

(SEQ ID NO: 7)
5'-CGCAGTCTTCTCCTGGTGCTCGAACAGTGAC-3';

(SEQ ID NO: 8)
3'-ACCACGAGCTTGTCACTG-5';

(SEQ ID NO: 9)
5'-CGCAGUCUUCUCCUGGUGCUCGAACAGUGAC-3;

(SEQ ID NO: 10)
3'-ACCACGAGCUUGUCACUG-5';

(SEQ ID NO: 11)
5'-GATAGCCATAGAGCCCTAGATAGCATTGGTGCTC
GAACAGTGAC-3';

(SEQ ID NO: 12)
3'-CTATCGGTATCTCGCTATCGTAACCACGAGCTTGTCACTG-5';

(SEQ ID NO: 13)
5'-GCACUGUAAAUGCAUUGCCAGAAACAACUGC-3';

(SEQ ID NO: 14)
3'-UAACGGUCUUUGUUGACG-5';

(SEQ ID NO: 15)
5'-TAGATAGCATTAGATAGCCACAGATAGCATCCTAGATAGC
ATTGGTGCTCGAACAGTGAC-3';
and (SEQ ID NO: 16)
3'-GTCTATCGTAGGATCTATCGTAACCACGAGCTTGTCACTG-5'.
```

Figure 11:
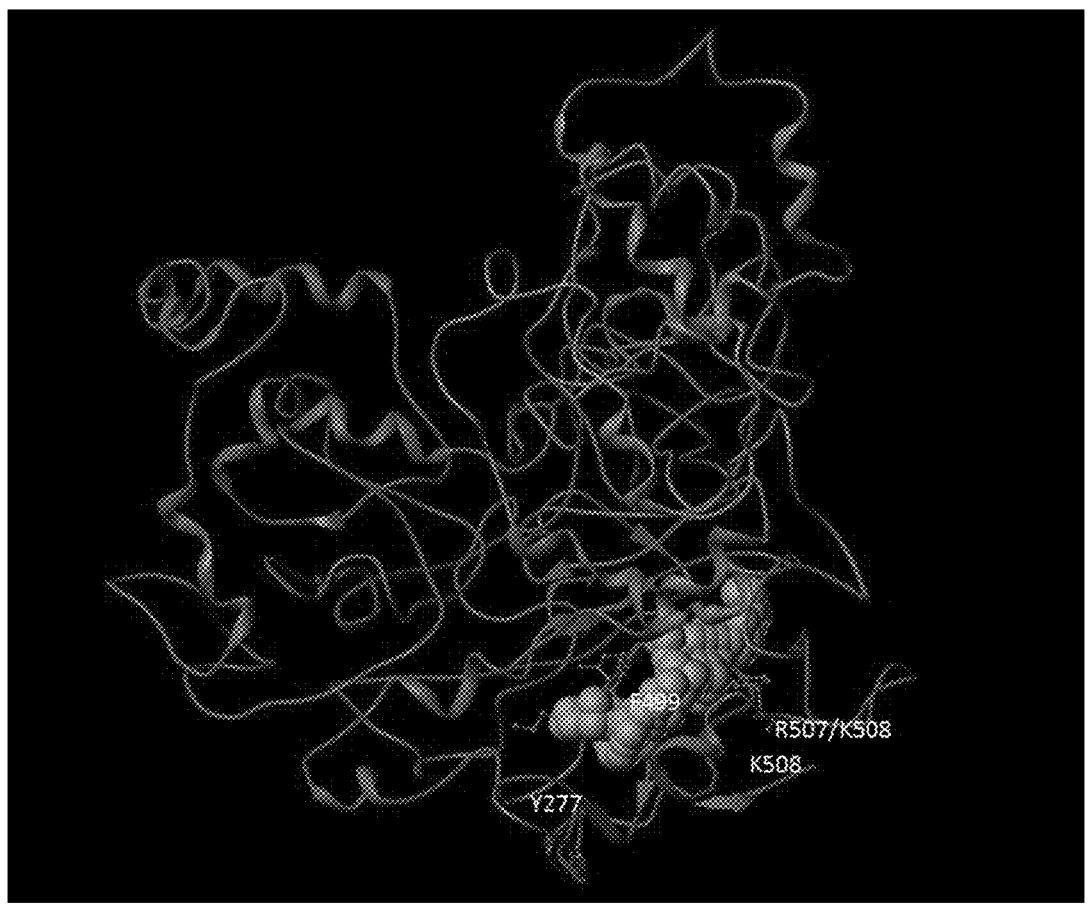

FIG. 11. SSYA10-001 binding pocket on SARS-CoV nsp13. Four residues (Y277, F499, R507 and K508) within nsp13 were predicted by Q-SiteFinder to contribute to the formation of the binding pocket for SSYA10-001.

Figure 12:
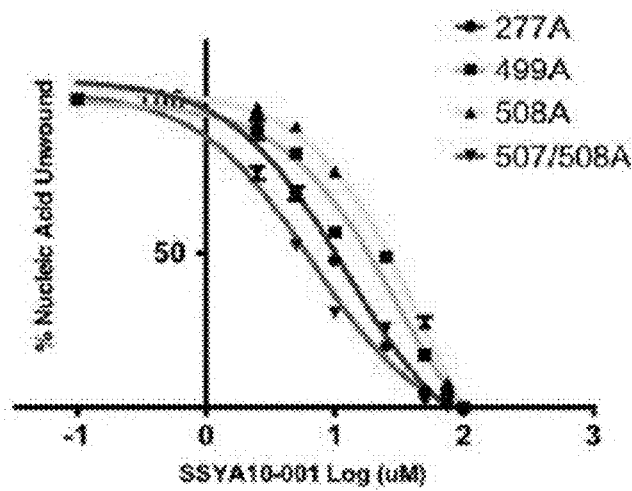

FIG. 12. Effect of SSYA10-001 on activity of SARS-CoV helicase mutants. Under the same conditions, the wild-type SARS-CoV nsp13 had a lower $IC_{50}$ of 6 μM (more susceptible than the mutants).

Figure 13:
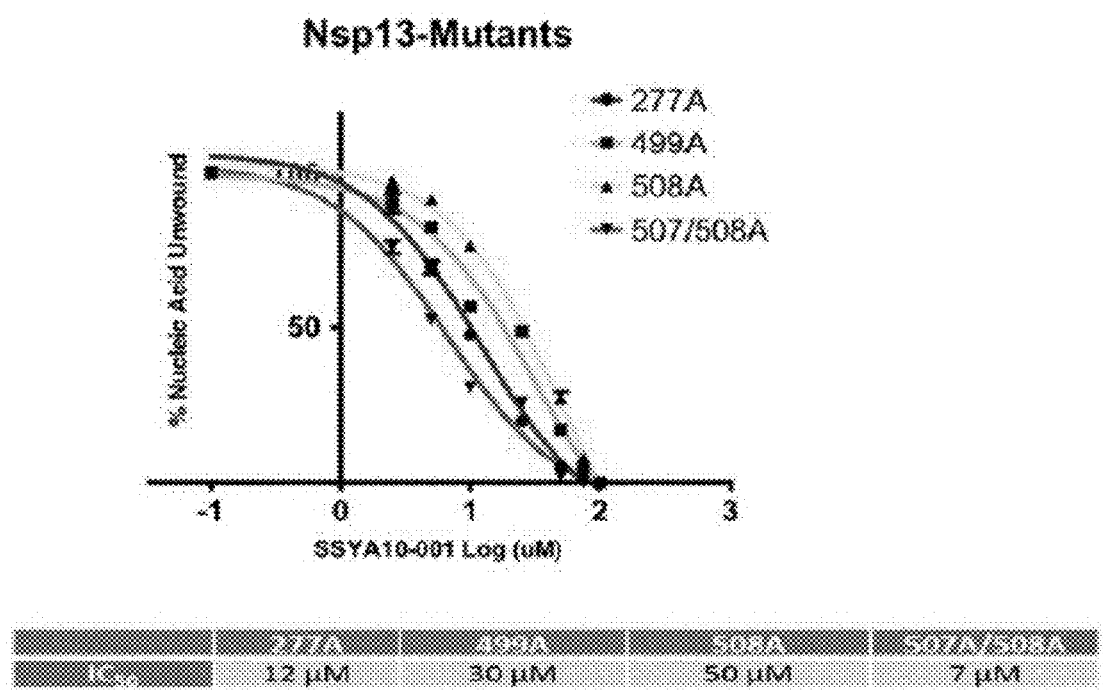

FIG. 13. Amino acid sequence alignment of SARS-CoV and MERS-CoV nsp13 helicases. The two proteins share 86% sequence homology. The Inhibitor binding site is highlighted in green. In red are residues of the corresponding active sites.

DETAILED DESCRIPTION OF INVENTION

Unless otherwise defined, all technical and scientific terms used herein have the same meaning as commonly understood by one of ordinary skill in the art to which this invention belongs. Any use of a singular term, such as the number one (1), is intended to encompass numerical values greater than one, such as represented by the phrase "one or more." Any use of inclusive terms such as "including" or "such as" and the like is intended to be open ended, with a meaning similar to "including, but not limited to." All publications, patent applications, patents, and other references mentioned herein are incorporated by reference in their entirety.

Disclosed herein is a potent inhibitor of SARS-CoV that is capable of blocking the replication of SARS-CoV by inhibiting the unwinding activity of the SARS-CoV helicase (nsp13).

SARS-CoV contains a single stranded, 5'-capped, polyadenylated positive strand RNA genome that is ~29.7 kb in size (34, 39). The first ORF (ORF1a/b) encompasses about two-thirds of the genome and codes for the replicase proteins. Following a −1 frame shift signal, translation continues in ORF1b after initiation at the ORF1a. The virally encoded chymotrypsin-like protease 3CLpro (also called Mpro or main protease) and the papain-like protease (PLP) cleave (auto-proteolysis) the newly-formed ORF1a and ORF1ab polypeptides, the pp1a and pp1ab, respectively, into 16 non-structural proteins including an NTPase/helicase that is known as non-structural protein 13 (nsp13). The present inventor recognized that helicases targets for antiviral therapies.

Helicases are motor proteins that unwind double-stranded nucleic acids (dsNA) into two single-stranded nucleic acids by utilizing the energy derived from nucleotide hydrolysis. Helicases may unwind dsDNA and/or dsRNA substrates and they could be active as a monomer or multimer. Helicases may also be involved in protein-protein interactions and interactions with host factors. The present inventors recognize that helicases are valid antiviral targets. Some inhibitors of helicases may also be competitive inhibitors at the ATP binding site or bind non-specifically at the nucleic acid binding cleft of other host cellular proteins, such as cellular kinases which are required for normal cellular metabolism.

Ideally, a compound that targets a viral helicase should block a viral replication without affecting cellular functions. For example, compounds that prevent binding of nucleic acid binding may interfere with the function of related cellular enzymes and would not be suitable for therapeutic purposes. In addition, compounds that might interfere with binding and/or hydrolysis of ATP may also interfere with the ATPase activity of other cellular ATPase or kinases and cause adverse side effects. In that respect, previously reported nsp13 inhibitors shown to interfere with both unwinding and ATPase activities of nsp13 are likely to impede normal cellular activities.

In order to identify an inhibitor of nsp13, a FRET-based helicase assay was used to screen the Maybridge Hitfinder Chemical library. A compound (SSYA10-001) that specifically blocked the double stranded (ds) RNA and dsDNA unwinding activities of nsp13 with an $IC_{50}$s of 5.70 and 5.30 µM, respectively was identified and validated. SSYA10-001 also exhibited inhibitory activity ($EC_{50}$=8.95 µM) in a SARS-CoV replicon assay with low cytotoxicity ($CC_{50}$=>250 µM), suggesting that the helicase plays a yet unidentified critical role in SARS-CoV life cycle. Moreover, it was demonstrated that SSYA10-001 is an efficient inhibitor of viral replication as demonstrated in a SARS-CoV replicon assay.

Enzyme kinetic studies on the mechanism of nsp13 inhibition revealed that SSYA10-001 acts as a non-competitive inhibitor of nsp13 with respect to the nucleic acid and ATP substrates. Moreover, SSYA10-001 did not affect ATP hydrolysis or nsp13 binding to the nucleic acid substrate. SSYA10-001 did not inhibit HCV helicase or other bacterial and viral RNA-dependent RNA polymerases and reverse transcriptase. These results show that SSYA10-001 specifically blocks nsp13 through a novel mechanism and that SSYA10-001 does not interfere with the functions of cellular enzymes that process nucleic acid or ATP. Hence, SSYA10-001 inhibits nsp13 unwinding by affecting conformational changes during the course of the reaction or translocation on the nucleic acid. In addition, SSYA10-001 is valuable for studying the specific role of nsp13 in SARS-CoV life cycle, and in a method or as a component of a antiviral composition for SARS or other nidoviruses.

Activity of SSYA10-001 against SARS-CoV replication was confirmed by demonstrating that SSYA10-001 reduced the levels of SARS-CoV RNA in replicon-transfected cells with an $EC_{50}$ of ~9 µM. (FIG. 8 and Table 1). Further cytotoxicity measurements indicated that the $CC_{50}$ for SSYA10-001 was higher than 250 µM. Since the antiviral activity of the compound is ~9 µM, the selectivity index ($CC_{50}/EC_{50}$) is ~30. SSYA10-001 is a derivative of triazole group. The present inventors recognize some derivatives of triazole have high bioavailability, with some of them demonstrating anti-inflammatory, antimycobacterial, antimicrobial, anticonvulsant and analgesic activities. The present inventors also recognize that a triazole-3-thione compound, which is closely related to SSYA10-001, is a potent antithyroid compound with low toxicity. The properties of closely related compounds of SSYA10-001 show that SSYA10-001 is promising drug and drugable lead as an effective antiviral agent, exhibiting good pharmakokinetics.

Derivatives may be generated or synthesized by exchanging chemical groups of SSYA10-001 or a precursor thereof. The derivatives may be subjected to assays to determine the biological activity of helicase inhibition. In addition, modification to the SSYA10-001 may be made to obtain derivatives with increased bioavailability, capability to cross membrane barriers, solubility, activity, or, e.g., stability. Derivatives may also be synthesized by, e.g., culturing a microorganism capable of producing an organic compound in a prescribed culture medium and reacting the organic compound obtained from the culture with SSYA10-001 or a precursor thereof and with an additional reagent. Derivatives may also be synthesized by any organic chemical methodology. A compound library of chemical compounds containing derivatives of SSYA10-001 or a precursor thereof can be constructed. Such library enables random high-throughput screening of derivatives with improved characteristics, e.g., bioavailability, activity, stability, etc.

In particular embodiments, 1,2,4-triazole derivatives for treatment of SARS-CoV and other coronaviruses are employed.

In certain embodiments, the compounds of the present inventions are derivatives of the formula II shown below:

Formula II

Basic structure of derivatives

In certain embodiments, B represents Sulfur or Oxygen;

In certain embodiments, X, Y, and Z are independently selected from one another from the group that consisting H, —SH, and —O—R.

In certain embodiments, R (of the O—R group) may be selected from the group consisting of H, alkyl, alkenyl, alkynyl, C3-C6 cyclo-alkyl, cyclo-alkyl-alkyl, aryl, hetero-aryl, aryl-alkyl, heteroaryl-alkyl, heterocyclyl, heterocycly-lalkyl, alkylsulfonyl, and arylsulfonyl. Any of these R groups may be independently substituted by up to 3 substituents from the following: halogen (—F, —Cl, —Br, —I) azido (—N3), cyano (—CN), hydroxyl (—OH), nitro (—NO2), alkyl, aryl, arylalkyl, —O-alkyl, and —O-aryl.

In certain embodiments, a triazole derivative can be 3-[(2-nitrophenyl)sulfanylmethyl]-4-prop-2-enyl-1H-1,2,4-triazole-5-thione (also called SSYA10-001, formula I).

Figures 4A, 4B:
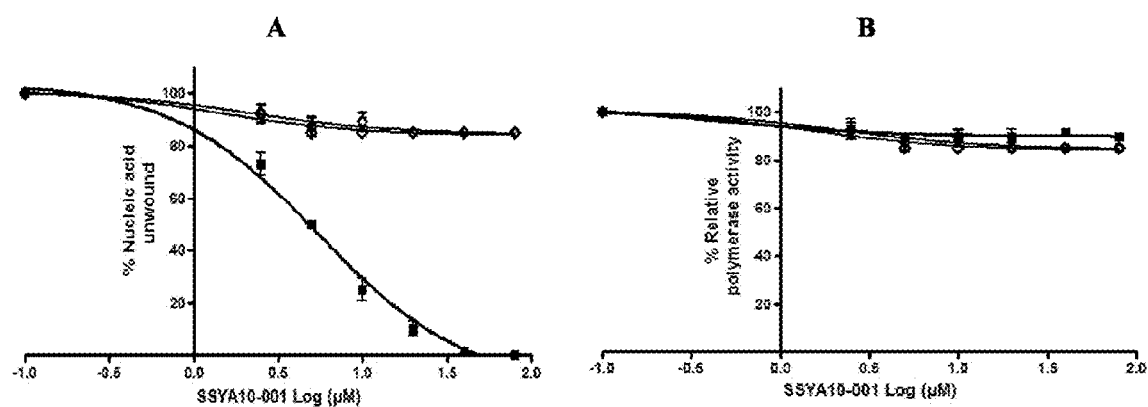
Figures 5A, 5B:
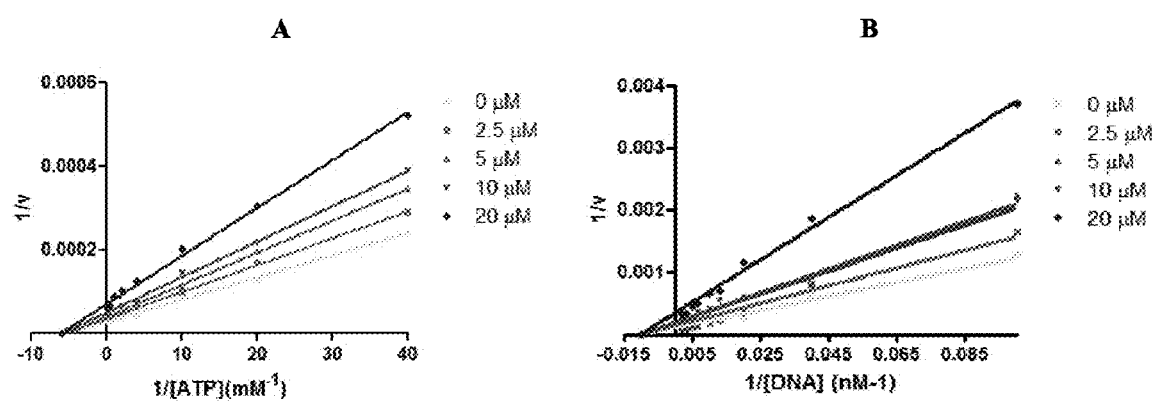

To determine the specificity of SSYA10-001 and to eliminate the possibility that it binds promiscuously other nucleic acid binding proteins, effect of SSYA10-001 on the enzymatic activities of several viral or bacterial polymerase and helicases was assessed. These included two other viral helicases (HCV NS3 and Dengue virus NS3), a retroviral reverse transcriptase (MoMLV RT) a viral RNA polymerase (FMDV-3D pol) and a bacterial DNA polymerase. The results demonstrated that SSYA10-001 was specific for SARS-CoV helicase inhibition (FIG. 4). Hence, SSYA10-001 did not bind non-specifically to dNTP or NTP binding pockets of polymerases, NTP-binding pockets of helicases, or nucleic acid binding domains of polymerases or helicases. These results were consistent with kinetic studies demonstrating that SSYA10-001 did not competitively inhibit the binding of nucleic acid and ATP to nsp13 (FIGS. 5A and 5B).

Since SSYA10-001 did not inhibit nsp13's binding and hydrolysis of nucleic acid and ATP and SSYA10-001 did not bind the nucleic acid substrate, the present inventors recognized that is likely that SSYA10-001 inhibited unwinding by affecting conformational changes during the course of the reaction or translocation on the nucleic acid.

Because of high homology between SARS coronavirus helicase and other coronavirus helicases (~70%, data not shown), SSYA10-001 may also inhibit other coronaviruses that cause human disease, including but not limited to HCoV-229E, NL63.

In certain embodiments, the compounds of the present invention are suitable to inhibiting virus replication, or treat or prevent a virus infection with a virus that has a helicase activity that can be inhibited with the compounds of the present invention.

According to one embodiment of the invention, disclosed herein is a method of inhibiting the replication of a virus comprising administering a compound with the core formula (I):

Formula (I)

SSYA10-001
($IC_{50}$ = 6 µM): 3-[(2-nitrophenyl)
sulfanylmethyl]-
4-prop-2-enyl-1H-1,2,4-triazole-
5-thione In certain embodiments, the compounds and methods of this invention were designed to be helicase inhibitors of Nidovirales viruses, such as Coronaviridae viruses, SARS viruses. In certain embodiments the viruses are HCoV-229E, or NL63. In certain embodiments, the virus is MERS-CoV.

In certain embodiments, the present invention also includes compositions comprising the compound or a pharmaceutically acceptable salt thereof, and/or and a pharmaceutically acceptable carrier.

If pharmaceutically acceptable salts of the compounds of this invention are utilized in these compositions, those salts may be derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

In certain embodiments, the compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The antiviral compositions provided herein may optionally include one or more additional components, such as carriers, stabilizers, immune system stimulating materials, disinfectants, chemically or otherwise inactivated viral material, or additional viral inhibitory compounds.

In certain embodiments, pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The antiviral compositions of the invention may be administered to the receiving subject in any medically effective manner, including enteral, parenteral, topical, transmucosal, intramuscular, intravenous, and inhalation delivery methods.

In certain embodiment, the compositions of this invention are formulated for pharmaceutical administration to an organism such as a mammal, or human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In certain embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica or similar alcohol. The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

In certain embodiments, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

When administered parenterally, the pharmaceutical composition may be formulated in a unit dosage injectable form (solution, suspension, emulsion) with at least one pharmaceutically acceptable excipient. Such excipients are typically nontoxic and non-therapeutic. Examples of such excipients are water, aqueous vehicles such as saline, Ringer's solution, dextrose solution, and Hank's solution and non-aqueous vehicles such as fixed oils (e.g., corn, cottonseed, peanut and sesame), ethyl oleate, and isopropyl myristate. Sterile saline is a preferred excipient. The excipient may contain minor amounts of additives such as substances that enhance solubility, isotonicity, and chemical stability, e.g., antioxidants, buffers, and preservatives. When administered orally (or rectally) the compounds will usually be formulated into a unit dosage form such as a table, capsule, suppository, or cachet. Such formulations typically include a solid, semi-solid or liquid carrier or diluent. Exemplary diluents and excipients are lactose, dextrose, sucrose, sorbitol, mannitol, starches, gum acacia, calcium phosphate, mineral oil, cocoa butter, oil of theobroma, alginates, tragacanth, gelatin, methylcellulose, polyoxyethylene, sorbitan monolaurate, methyl hydroxybenzoate, propyl hydroxybenzoate, talc and magnesium stearate. In preferred embodiments, the pharmaceutical composition according to the invention is administered intravenously.

In certain embodiments, the pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

In certain embodiments, topical application for the lower intestinal tract can be effected in a rectal suppository formulation or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

In certain embodiments, the pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound present in the above-described composition should be sufficient to cause a detectable decrease in activity of the viral helicase, as measured by any of the assays described in the examples.

It should also be understood that a specific dosage and treatment regimen for any particular patient will depend upon a variety of factors, including the activity of the pharmaceutical composition, the age, body weight, general health, sex, diet, time of administration, rate of excretion, drug combination, and the judgment of the treating physician and the severity of the particular disease being treated. The amount of active ingredients will also depend upon the particular compound and anti-viral agent, if present, in the composition.

The dosage ranges for administration of SSYA10-001 or derivatives thereof to a subject, are those which produce the desired affect whereby symptoms of infection are ameliorated. In particular, the compounds of the present invention are effective against Nidovirales viruses that comprise a helicase susceptible for SSYA10-001 or derivatives thereof. For example, as used herein, a pharmaceutically effective amount for a Nidovirales virus infection refers to the amount administered so as to maintain an amount which suppresses or inhibits circulating virus throughout the period during which infection is evidenced such as by presence of anti-viral antibodies, presence of culturable virus and presence of viral antigen in patient sera, or symptoms that are identifiable by a medical professional. The presence of anti-viral antibodies can be determined through use of standard ELISA or Western blot assays for example.

The dosage will generally vary with age, extent of the infection, the body weight and counter indications, if any, for example, immune tolerance. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage may vary, for example, from between about 0.001 mg/kg/day to about 150 mg/kg/day, or optionally between about 1 to about 50 mg/kg/day.

In certain embodiments, the invention provides for methods of treating an organism suspected of having a Nidovirales virus infection such as a SARS infection. In certain aspects such method may include steps for identifying organisms suspected of having a Nidovirales virus infection. Such identification can be conducted by diagnostic procedures specific for the particular viral infection. This may include detecting symptoms of the virus infection, and detecting virus-specific antigens, antibodies, or nucleic acids in a biological sample. The term "biological sample," as used herein may include cell cultures or extracts thereof; biopsied material obtained from a mammal or extracts thereof; and blood, saliva, urine, feces, semen, tears, or other body fluids or extracts thereof. The term "biological sample" also includes living organisms.

In certain embodiments, the invention provides for methods for administering the pharmaceutical composition of the present invention to organism that are suspected to have been or will be exposed to Nidovirales virus.

In certain embodiments, the components or pharmaceutical compositions of the present invention provide prophylactic and/or therapeutic effects almost immediately upon administration.

EXAMPLES

Example 1

96-Well Plate FRET-Based Helicase Assay

To monitor the unwinding activity of nsp13, a fluorescence assay was employed. This assay utilized a dsDNA substrate with two chromophores (fluorescein-donor and black hole quencher-acceptor) placed on opposite strands but near each other on 5' and 3' ends of each strand (FIG. 1). An active helicase separates the two strands, and fluorescence signal is observed as a result of photon emission from the fluorescein chromophore (FAM). No fluorescence is observed if there is no strand separation because the emitted photons from the fluorescein are absorbed by the black hole quencher (BHQ), thereby preventing the detection of fluorescein signals. The sequence of the reaction is as shown in FIG. 1. Fluorescence signals were detected at 520 nm (excitation at 495 nm). To assess the quality of this assay, the Z-factor was determined to be 0.66 under the experimental conditions. This value suggests this is an excellent assay as described by Zhang et al (Zhang, J. H., T. D. Chung, and K. R. Oldenburg. 1999. A Simple Statistical Parameter for Use in Evaluation and Validation of High Throughput Screening Assays. J Biomol Screen 4:67-73.).

Example 2

Chemical Library Screening

Figures 2A, 2B:
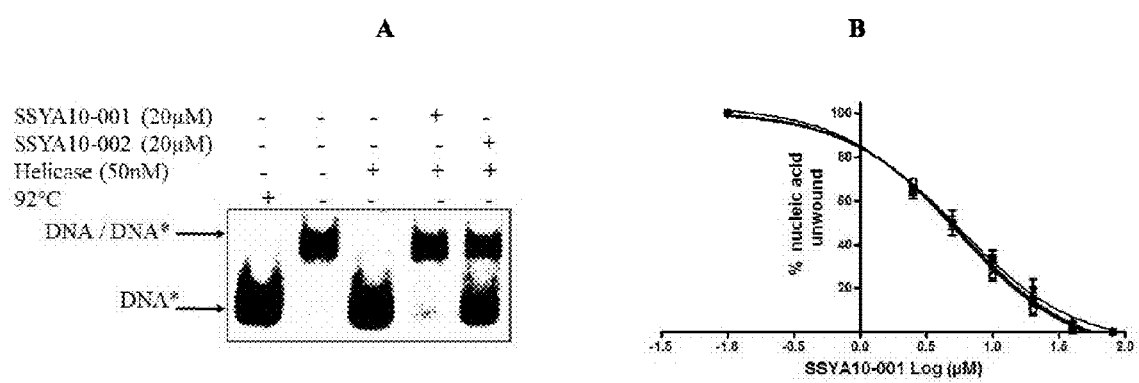
Figure 3:
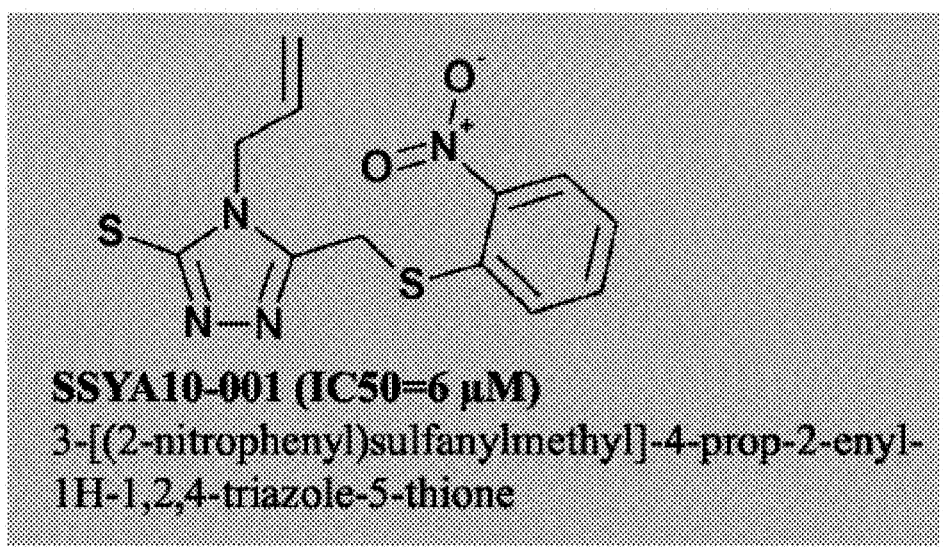

Using the assay described above, ~3,000 compounds were screened from the Maybridge HitFinder chemical library and only two compounds (SSYA10-001 and SSYA10-002) that suppressed fluorescence by >50% were selected. Such hits may include compounds that affect fluorescence of fluorescein and, as a consequence, appear as false positives. To rule out such false positives, the compounds' ability to specifically inhibit nsp13 unwinding activity in a gel-based assay that utilizes fluorescently labeled nucleic acid was evaluated. It was found that SSYA10-001 inhibited the nucleic acid unwinding activity of nsp13 (FIG. 2) with almost 100% inhibition of the helicase activity at 20 μM SSYA10-001. SSYA10-002 was considerably less potent. Hence, SSYA10-001 was further characterized with respect to nsp13 unwinding activity. The chemical structures and the names of these compounds are shown in FIG. 3.

Example 3

Effect of SSYA10-001 on Nsp13 Unwinding Activity of dsRNA Substrate

Since Nsp13 can unwind equally well dsRNA and dsDNA and since RNA is the biological substrate of nsp13, the effect of SSYA10-001 on the nsp13 unwinding activity of dsRNA (31/18-mer) and SARS-CoV specific dsRNA was monitored. As shown in FIG. 2B and Table 1, SSYA10-001 exhibited similar $IC_{50}$s for the inhibition of nsp13 dsRNA (31/18-mer), dsDNA (31/18-mer) and SARS-CoV specific dsRNA unwinding activities ($IC_{50}$s of 5.70, 5.30 and 5.60 μM, respectively).

TABLE 1

| $IC_{50}$ and $CC_{50}$ values of SSYA10-001 | | | | |
|---|---|---|---|---|
| $IC_{50}$ (μM) | | | | |
| RNA | DNA | SARS-CoV RNA | $EC_{50}$ (μM) Replicon (RT-qPCR) | CC50 (μM) |
| 5.7 ± 0.74 | 5.3 ± 0.40 | 5.6 ± 0.50 | 8.95 ± 0.86 | >250 |

$IC_{50}$ values in Table 1 were determined from the helicase gel-based assay; $EC_{50}$ and $CC_{50}$ values were determined from the replicon cell-based assay. All values were obtained by using the dose response curve in GraphPad Prism 5.0 (GraphPad Inc.). Experiments were performed three times and the values represent mean±standard deviation.

Example 4

SSYA10-001 Inhibits Specifically SARS-CoV Helicase

To determine if SSYA10-001 was specific for nsp13 inhibition, the effect of SSYA10-001 on SARS-CoV nsp13, Hepatitis C Virus (HCV) NS3h and Dengue Virus NS3 helicases was monitored and compared. The result in FIG. 4A shows that SSYA10-001 inhibition of helicase activity is specific for SARS-CoV helicase. Moreover, SSYA10-001 did not cause inhibition of RNA and DNA polymerases, including FMDV 3Dpol, MoMLV Reverse Transcriptase, and KF. (FIG. 4B)

Example 5

Kinetic Mechanism of Inhibition

To establish the mode of inhibition of nsp13 by SSYA10-001, the kinetic mechanism of inhibition and $K_i$ value was determined. The Lineweaver-Burk plots in FIGS. 5A and 5B comprise of a series of five lines (one for each inhibitor concentration) intersecting at the same point on the X-axis ($-1/K_m$), which is a hallmark of non-competitive inhibition. Hence, nsp13 inhibition by SSYA10-001 was non-competitive with respect to both the ATP and the nucleic acid substrates. The $K_i$ value for SSYA10-001 obtained from the Dixon plot (1/V vs. [SSYA10-001], not shown) was 6.0±1.7 μM.

Example 6

SSYA10-001 does not Prevent DNA Binding and ATP Hydrolysis by SARS-CoV Nsp13

Figures 6A, 6B:
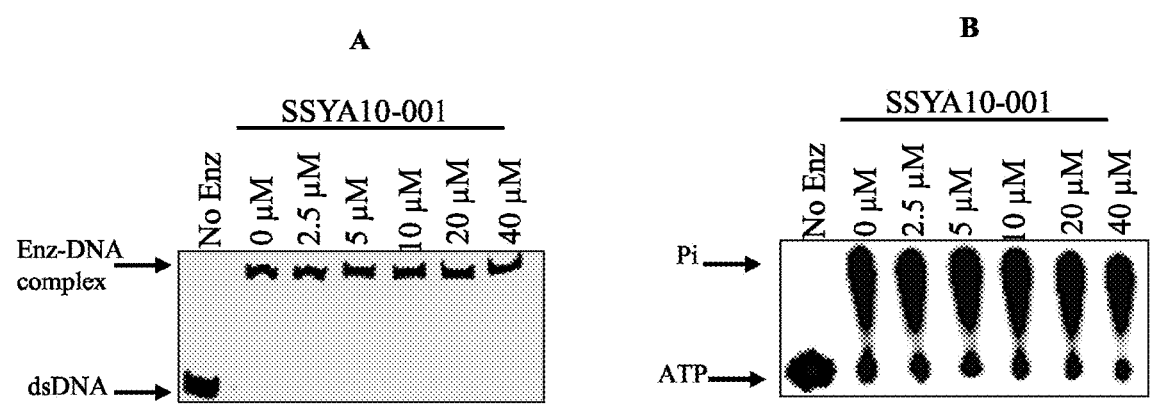

To determine whether SSYA10-001 inhibits the unwinding activity of nsp13 by interfering with nsp13's nucleic acid binding capability, the DNA binding of nsp13 was monitored in the presence and absence of varying concentrations of SSYA 10-001, and analyzed the reaction using a gel-shift mobility assay. As shown in FIG. 6A, SSYA10-001 did not affect the ability of nsp13 to bind DNA. Similarly, the ATP hydrolysis of nsp13 was assessed with increase in the concentration of SSYA10-001. The results showed that hydrolysis of ATP by nsp13 was not inhibited by SSYA10-001 (FIG. 6B).

Example 7

SSYA10-001 does not Chelate Double-Stranded Nucleic Acid (dsNA)

Figures 7A, 7B, 7C, 7D:
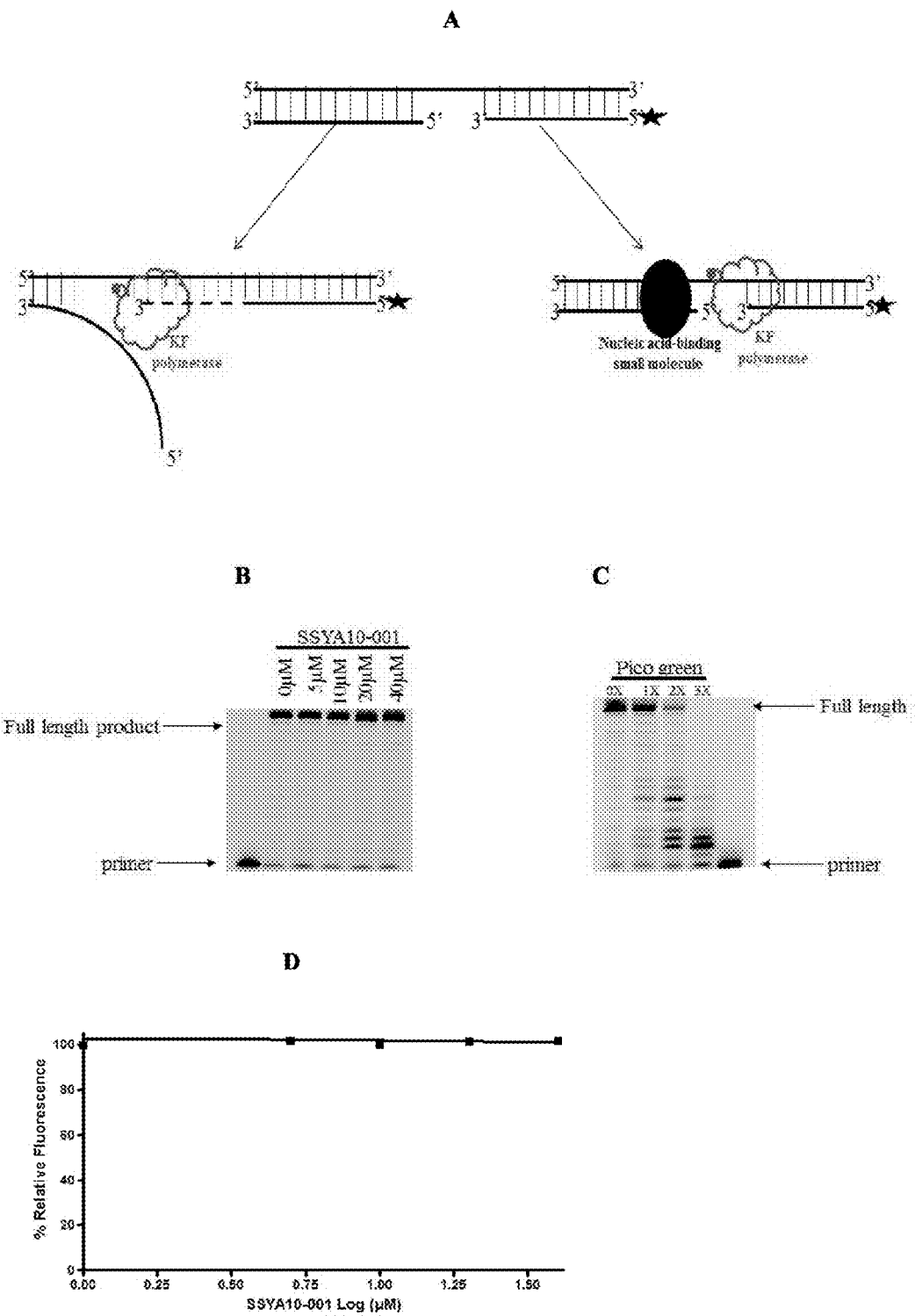

To rule out the possibility of SSYA10-001 binding the nucleic acid substrate, a gel-based primer extension-strand displacement assay was performed. A blocker substrate as shown in FIG. 7A with a 14 nt long complementary strand acting as the blocker at the 5' end of the template strand was designed. Then, a primer extension assay was performed with and without SSYA10-001, with Klenow fragment of E. coli DNA polymerase I (KF), which has both polymerase and strand displacement activities. The results in FIG. 7B demonstrated that SSYA10-001 did not prevent KF from its polymerization and strand displacement activities. This demonstrated that SSYA10-001 did not bind nucleic acid. To validate this assay, the same experiment as described above was conducted, except that SSYA10-001 was replaced with pico green as a positive control, a known nucleic acid chelator. The result in FIG. 7C showed that pico green interfered with the ability of the KF to extend the primer and displace the blocker strand because of pico green's DNA chelating (minor groove binding) ability. To further evaluate the possibility of SSYA 10-001 binding to DNA, varying concentrations of the SSYA10-001 (0, 2.5, 5, 10, 20 and 40 µM) were preincubated with dsDNA (31/18-mer) for 10 minutes followed by addition of 1× final concentration of pico green reagent, and immediate fluorescence measurement. The fluorescent counts from pico green interaction with the dsDNA did not change with increasing concentrations of SSYA10-001 suggesting that SSYA10-001 did not bind DNA (FIG. 7D).

Example 8

Inhibition of SARS-CoV Replication by SSYA10-001

To monitor the effect of SSYA10-001 on the replication of SARS-CoV, SARS-CoV replicon assays were performed. The SARS-CoV replicon and the non-replicative construct (NRC) were cloned in a pBAC plasmid which contained a CMV promoter. To eliminate the possibility of SSYA10-001 inhibiting RNA pol II/CMV promoter, varying concentrations of SSYA10-001 were added to the NRC-transfected cells. No difference was observed between the amount of RNA synthesized in the presence and absence of SSYA10-001 in the NRC-transfected cells. Hence, the DNA amplicon measured from the non-replicative construct was regarded as the background, and as a result, the amount of DNA amplified from the SARS-CoV replicon was normalized with the quantified DNA amplicon from the non-replicative construct after normalization of all samples to the cycle threshold (CT) counts of the housekeeping gene, U6, as a control. The average raw CT counts of the SARS-CoV replicon without compound was ~21 compared to an average of ~28 for the NRC before normalizing to the CT counts of U6 (~18). Following the normalization to U6 with additional normalization to NRC and using the equation ($2^{-\Delta\Delta CT}$) to obtain the relative quantity (RQ), the amount of DNA amplified from the SARS-CoV replicon was ~100 fold in excess over the DNA amplicon from the non-replicative construct (NRC). These experiments with the SARS-CoV replicon were performed in the presence and absence of varying concentrations of SSYA10-001. As shown in FIG. 8A and Table 1, SSYA10-001 inhibits SARS-CoV replication with an $EC_{50}$ of 8.95 μM. To confirm this result, a RNAse protection assay (RPA) was performed to further monitor the amount of RNA synthesized in the presence of varying concentrations of SSYA10-001. As shown in FIG. 8B, SSYA10-001 interfered with SARS-CoV replication.

The RNase Protection Assay (RPA) was carried out as follows. Total RNA was obtained as described above. The RNase Protection probes were generated by cloning SARS-CoV fragments from nucleotides (nt) 7281 to 7431 (total of 150 nt) into the EcoRI and XbaI restriction sites of T7/Sp6-driven pGEM-3Z transcription vector (Promega) followed by transcript generation through Sp6-controlled in vitro transcription with NTPs and radioactive UTP incorporation to obtain an antisense probe (See Mouw, M. B., and D. J. Pintel. 2000. Aden o-associated virus RNAs appear in a temporal order and their splicing is stimulated during coinfection with adenovirus. J Virol 74:9878-9888; and Schoborg, R. V., and D. J. Pintel. 1991. Accumulation of MVM gene products is differentially regulated by transcription initiation, RNA processing and protein stability. Virology 181:22-34). The antisense probe generated was 182 nt long because of the extra 32 nt between Sp6 transcription start site and XbaI site of the pGEM-3Z vector. This was followed by DNase I treatment and RNA isolation using phenol-chloroform RNA extraction protocol. RPAs were performed at 55° C. by overnight annealing of the newly generated probes with each of the total intracellular RNA samples containing different concentrations of SSYA10-001. This was followed by RNase A and T1 treatment of the annealed reactions. The reaction samples were analyzed on a 6% Urea-PAGE and visualized using the phosphorimager (FLA 5000, FujiFilm).

Example 9

Evaluation of Cytotoxicity

SSYA10-001 was evaluated for its effect on cell viability using the XTT cell viability assay. HEK293T cells were incubated with varying concentrations of SSYA10-001 for 48 hours. No cytotoxicity was observed for SSYA10-001 at 250 μM concentration (Table 1). It was therefore calculated that the 50% cytotoxic concentration ($CC_{50}$) of SSYA10-001 is >250 μM. To investigate the cytostatic effect of SSYA10-001, a cytostatic assay was carried out, and as shown in FIG. 9, SSYA10-001 did not interfere with the proliferation of HEK293T cells.

The cell cytostatic assay was carried out as follows: To assess the cytostatic effect of the compound, $7.5\times10^5$ cells/well of HEK 293T cells were seeded in 6-well plates and the cells were maintained in a final volume of 2 ml DMEM medium with 10% FBS and 50 μg/mL of penicillin G and streptomycin. 250 μM of SSYA10-001 was added to each well and the medium was changed every daily and fresh compound was added each time. The cells were collected at 0, 12, 24 and 48 hrs, and viability was determined by trypan blue exclusion method and counted on a hemocytometer (See Periyasamy-Thandavan, S., S. Takhar, A. Singer, M. R. Dohn, W. H. Jackson, A. E. Welborn, D. Leroith, M. Marrero, M.

Thangaraju, S. Huang, and P. V. Schoenlein. 2012. Insulin-like growth factor 1 attenuates antiestrogen- and antiprogestin-induced apoptosis in ER+ breast cancer cells by MEK1 regulation of the BH3-only pro-apoptotic protein Bim. Breast Cancer Res 14:R52). To perform the tryptan blue exclusion method, cell samples were diluted in a 0.4% Trypan Blue solution at 1:1 dilution. Blue-colored cells were regarded non-viable while the viable cells were unstained. The number of viable cells counted was plotted against time using the Graphpad Prism 5.0 (GraphPad Inc.). Experiments were performed in triplicates.

Example 10

Identification of SSYA10-001 Binding Site in SARS-CoV Nsp13

The Q-SiteFinder (See Adedeji A O, Singh K, Sarafianos S G, Structural and biochemical basis for the difference in the helicase activity of two different constructs of sars-cov helicase, *Cell Mol Biol* 58: 114-12 (2012)) was used to predict a ligand-binding site on nsp13 that could be the binding site for SSYA10-001. A Q-SiteFinder analysis determines energetically favorable ligand-binding sites on the surface of a protein. This method is able to predict binding sites based on volumes roughly equivalent to ligand volumes irrespective of the overall size of the protein (See, Alasdair, T. R., Jackson, L., Jackson M. R., Q-SiteFinder: an energy-based method for the prediction of protein-ligand binding sites, Oxford Journals 21: 1908-1906 (2005)). The potential ligand-binding site in SARS-CoV nsp13 comprises amino acid residues Y277, F499, R507, and K508 (FIG. 11).

Example 11

Validation of SSYA10-001 Binding Site in SARS-CoV Nsp13

To assess the prediction regarding the SSYA10-001 binding pocket, site-directed mutagenesis was performed at the residues in the pocket to change these to alanines. For this purpose, Y277A, F499A, K508A, and the double mutant R507A/K508A nsp13s were cloned. The mutant enzymes were purified in active forms and their susceptibility to SSYA10-001 was evaluated using a FRET-based assay. See, Adedeji A O, Singh K, Calcaterra N, DeDiego M, Enjuanes L, Weiss S, Sarafianos S G, SARS-CoV Replication Inhibitor that Interferes with the Nucleic acid Unwinding of the Viral Helicase, *Antimicrob Agents Chemother* 56, 4718-28 (2012)). It was hypothesized that changes in the interactions between SSYA10-001 and the altered residues would result in decreases in inhibitor binding and thus decreased susceptibility to inhibition by SSYA10-001. Indeed, results in FIG. 12 demonstrate that SSYA10-001 inhibits the mutants with decreased potencies, as determined by the estimated $IC_{50}$ values. When WT-nsp13 ($IC_{50}$ of 6 µM) and the nsp13 site-directed mutants were compared, the site-directed mutants (277A, 499A, 508A) showed a 2-fold, 5-fold, and 10-fold resistance, respectively, against SSYA10-001. Hence, the results demonstrate that this is the binding site of SSYA10-001.

Example 12

Sequence Alignment of SARS-CoV and HCoV-EMC (or MERS-CoV) Nsp13 Helicases Shows High Sequence Homology As shown in the sequence alignment in FIG. 13, there is a very strong similarity between the nsp13 helicases of the SARS-CoV and MERS-CoV viruses (86% sequence homology). Moreover, residues of the proposed SSYA10-001 binding site of SARS-CoV are conserved in MERS-CoV. This conclusively demonstrates that MERS-CoV can be inhibited by SSYA10-001 or its analogs, or derivatives.

Example 13

Materials and Methods

A. Materials

The Maybridge-Hitfinder chemical library of compounds (version 6) was purchased from Maybridge, (Thermo Fisher Scientific, Cornwall, United Kingdom). Screening reactions were carried out in Microfluor 2 black U-bottom 96-well plates (Fisher Scientific). Compound hits were also purchased independently from Ryan Scientific Inc. (Mt. Pleasant, S.C.) for independent validation of the inhibition results. Synthetic oligonucleotides were purchased from Integrated DNA Technologies (Coralville, Iowa). Sequences of the DNA and/or RNA substrates are shown in FIG. 10.

Concentrations were determined spectrophotometrically using absorption at 260 nm and their extinction coefficients. For the screening assay, the fluorescein-labeled oligonucleotide was annealed with the BHQ-labeled oligonucleotide at a ratio of 1:1.2 in 50 mM Tris pH 8.0, 50 mM NaCl at a ratio of 1:1.2 by heating at 95° C. for 5 minutes and cooling slowly to room temperature. For the gel-based assay, unlabeled oligonucleotide was annealed to the corresponding 5'-Cy3 labeled 28-mer in similar conditions as described previously.

B. Cloning, Expression and Purification of Nsp13

The cloning, expression and purification of nsp13 was as previously described (Adedeji, A. O., B. Marchand, A. J. Te Velthuis, E. J. Snijder, S. Weiss, R. L. Eoff, K. Singh, and S. G. Sarafianos. 2012. Mechanism of Nucleic Acid Unwinding by SARS-CoV Helicase. PLoS One 7:e36521). Briefly, nsp13 was prepared either with a GST or with a $His_6$ tag. GST-nsp13 was expressed in a baculovirus expression system and purified using glutathione Sepharose beads (Amersham Biosciences) followed by gel filtration using a Superdex 200 column (GE Healthcare). The inhibitors blocked the activity of both enzymes with the same $IC_{50}$s.

C. Hepatitis C Virus (HCV) NS3h Protein Expression and Purification

The recombinant plasmid pET21-NS3HCV was provided by Professor Charles Rice (Rockefeller University). Expression of NS3h in BL21 (DE3) *E. coli* was induced by 1 mM isopropyl-1-thio-β-D-galactopyranoside for 3 hrs at 37° C. The cells were harvested and the cell pellet from a 1 L culture was incubated with 40 ml lysis buffer (50 mM Tris-HCl, pH 7.8, 500 mM NaCl, 1 mM phenylmethylsulfonyl fluoride (PMSF), 0.1% NP-40, 1% sucrose and 2 mg/ml lysozyme), then sonicated and centrifuged at 15,000 g for 30 min. The supernatant was diluted 2-fold in Buffer A (50 mM Tri-HCl pH 7.8, 1 mM PMSF, 4% streptomycin sulfate and 10% sucrose), stirred on ice for 30 min and centrifuged. The supernatant was loaded on a Ni-NTA column and bound proteins were washed with 20 ml Buffer B (20 mM Tris-HCl pH 7.5, 500 mM NaCl) and 5 mM imidazole, followed by 20 ml Buffer B with 75 mM imidazole.

NS3h was eluted in 2 ml fractions with 20 ml buffer B containing 300 mM imidazole. Fractions with NS3h were pooled and further purified by size exclusion chromatography (Superdex 75; GE Healthcare). The resulting protein was >90% pure, as determined by SDS-PAGE with Coomassie Blue staining. The protein was stored in 20 mM Tris-HCl pH 7.5, 100 mM NaCl, 1 mM DTT and 5% glycerol at −80° C.

D. Dengue Virus Helicase NS3 Protein Expression and Purification

The pDest17-H$_6$-NS3 plasmid was obtained from Dr. Bruno Canard's Lab in AFMB, Universités d'Aix-Marseille France and the expression of His$_6$-NS3 protein was performed in *E. coli* BL21(DE3)/pDNAy and purified as follows. One-liter culture of *E. coli* BL21(DE3)/pDNAy/pDest17-NS3 containing 100 μg/ml ampicillin and 50 μg/ml kanamycin were grown to OD$_{600}$=0.5 at 37° C. 2% ethanol was added to the culture followed by induction with 50 μM IPTG, chilled on ice for 2 h and then incubated at 17° C. overnight. Protein expression and purification was performed as described previously using Talon beads (See Tanner, J. A., R. M. Watt, Y. B. Chai, L. Y. Lu, M. C. Lin, J. S. Peiris, L. L. Poon, H. F. Kung, and J. D. Huang. 2003. The severe acute respiratory syndrome (SARS) coronavirus NTPase/helicase belongs to a distinct class of 5' to 3' viral helicases. J Biol Chem 278:39578-39582). The protein was eluted with 25 mM Hepes, pH 7.0, 0.5 M NaCl, 200 mM imidazole, 0.1% Triton X-100. It was further purified on a Superdex75 10/300GL column (20 mM Tris-HCl, pH 6.8, 200 mM NaCl, 1 mM dithiothreitol (DTT), and 5% glycerol. Fractions containing the desired protein were concentrated and stored at –80° C.

E. Klenow Fragment (KF) *E. coli* Expression and Purification

The cloning, expression and purification was as described elsewhere (See Singh, K., and M. J. Modak. 2003. Presence of 18-A long hydrogen bond track in the active site of *Escherichia coli* DNA polymerase I (Klenow fragment). Its requirement in the stabilization of enzyme-template-primer complex. J Biol Chem 278:11289-11302). Briefly, the Klenow fragment plasmid DNA (pET28-H$_6$-KF) was used to transform *E. coli* CJ376. An overnight inoculum of the expression strain was added to 500-ml LB broth at 30° C. At A$_{595}$=0.3, to heat induce overproduction of the enzyme the incubation temperature was raised to 42° C. and cells were further grown for 4 hrs. Cells were harvested, washed, and resuspended in cell lysis buffer (50 mM Tris-HCl pH 8.0, 500 mM NaCl, 1 mM PMSF) containing 2 mg/ml lysozyme. Following sonication and centrifugation of the cell suspension (14,000 rpm for 30 min), the supernatant was passed through a DEAE column to remove DNA. The flow-through was fractionated with ammonium sulfate, using 60 and 85% saturations. The pellet obtained with 85% ammonium sulfate was resuspended in 5 ml of buffer I (50 mM Tris-HCl, pH 7.0, 1 mM DTT, 1 mM EDTA), dialyzed overnight against 1 liter of the same buffer, and applied to a Bio-Rex 70 column prewashed with Buffer I. The bound protein was eluted by 50-500 mM linear gradient of NaCl in Buffer I. Peak fractions (representing a 68-kDa protein on SDS-PAGE) were pooled, concentrated, and buffer exchanged in 50 mM Tris-HCl, pH 7.0, 1 mM DTT, 100 mM NaCl, added 30% glycerol and stored at –20° C.

F. Expression, Purification and Gel-Based Primer Extension Assay of Moloney Murine 9 Leukemia Virus Reverse Transcriptase (MoMLV-RT) and Foot-and-Mouth Disease Virus 3D-Polymerase (FMDV-3D Pol)

Expression, purification and gel-based primer extension assay of MoMLV-RT and FMDV-3Dpol were carried out as previously described (See Durk, R. C., K. Singh, C. A. Cornelison, D. K. Rai, K. B. Matzek, M. D. Leslie, E. Schafer, B. Marchand, A. Adedeji, E. Michailidis, C. A. Dorst, J. Moran, C. Pautler, L. L. Rodriguez, M. A. McIntosh, E. Rieder, and S. G. Sarafianos. 2010. Inhibitors of foot and mouth disease virus targeting a novel pocket of the RNA-dependent RNA polymerase. PLoS One 5:e15049; and Ndongwe, T. P., A. O. Adedeji, E. Michailidis, Y. T. Ong, A. Hachiya, B. Marchand, E. M. Ryan, D. K. Rai, K. A. Kirby, A. S. Whatley, D. H. Burke, M. Johnson, S. Ding, Y. M. Zheng, S. L. Liu, E. Kodama, K. A. Delviks-Frankenberry, V. K. Pathak, H. Mitsuya, M. A. Parniak, K. Singh, and S. G. Sarafianos. 2012. Biochemical, inhibition and inhibitor resistance studies of xenotropic murine leukemia virus-related virus reverse transcriptase. Nucleic Acids Res 40:345-359).

G. 96-Well Plate FRET-Based Screening Assay

The Maybridge-Hitfinder chemical library of compounds was screened using a Förster Resonance Energy Transfer (FRET)-based assay. The chemical library was supplied as lyophilized films in a 96-well plate format. A Precision Microplate Pipetting system (Winooski, Vt.) was used to suspend the compounds in 100% dimethyl sulfoxide (DMSO) to a final concentration of 10 mM ('mother plates'). From these plates several sets of 'daughter plates' containing 500 μM of each compound (in 100% DMSO) were generated and stored at –80° C.

The helicase reactions that generate fluorescence were carried out in a 96-well format. Specifically, each well contained 25 μl of reaction mixture containing 20 mM HEPES, 20 mM NaCl, 0.01% BSA, 2 mM DTT, 5% glycerol, 5 mM MgCl$_2$, and 50 nM nsp13 and 20 μM inhibitor. The helicase reaction was initiated by the addition of 100 nM fluorescein and black hole quencher-dsDNA), 0.5 mM ATP and 2 μM unlabeled ssDNA with sequence complementary to the BHQ-labeled DNA strand. The reactions were allowed to proceed for 10 min at 30° C. The change in fluorescence (excitation 495 nm, emission 520 nm) was measured immediately with a Quanta Master QM-1 T-format fluorescence spectrometer (Photon Technology International, Princeton, N.J.).

H. Gel-Based Helicase Assay

Helicase activity was measured by pre-incubating 50 nM nsp13 or 100 nM HCV NS3h or Dengue Virus NS3 with varying concentrations of the compound (0 μM, 2.5 μM, 5 μM, 10 μM, 20 μM and 40 μM) followed by incubation with 100 nM forked substrate (dsRNA or dsDNA) or 31/18-mer (13ss:18ds) (dsDNA or dsRNA) or SARS-CoV specific dsRNA with the longer strand designed from 7281 nt-7311 nt of SARS-CoV genome (FIG. 10) in a reaction buffer containing 20 mM HEPES, pH 7.5, 20 mM NaCl, 1 mM DTT, 0.1 mg/ml BSA, 5 mM MgCl2, and 2 mM ATP at 30° C. for 10 min for nsp13 (See Ivanov, K. A., V. Thiel, J. C. Dobbe, Y. van der Meer, E. J. Snijder, and J. Ziebuhr. 2004. Multiple enzymatic activities associated with severe acute respiratory syndrome coronavirus helicase. J Virol 78:5619-5632) or a reaction buffer containing 20 mM MOPS-NaOH, pH 7.0, 5 mM magnesium acetate, 5 mM ATP and 0.1 mg/ml BSA at 30° C. for 30 min for NS3h (See Levin, M. K., and S. S. Patel. 1999. The helicase from hepatitis C virus is active as an oligomer. J Biol Chem 274:31839-31846). The reaction mixture also contained 2 μM unlabeled 18-mer DNA/RNA as trap. Reactions were quenched by the addition of equal volume of loading buffer (100 mM EDTA, 0.2% SDS and 20% glycerol). Unless otherwise indicated, reactant concentrations refer to the final concentration in the reaction mixture. The released ssDNA or RNA product and unwound dsDNA or dsRNA) were resolved on a 6% non-denaturing-PAGE (polyacrylamide gel electrophoresis) using a running buffer containing 89 mM Tris-Borate, pH 8.2, and run for 2 hrs at 40 C and 150 V. The controls for measuring maximum unwinding were dsDNA denatured by heating for 5 min at 95° C. and loading immediately on the gel as suggested by Ahnert et al. (See Patel, S. S. 2009. Structural biology: Steps in the right direction. Nature 462:581-583.). In this and subsequent assays, the gels were scanned with a phosphorimager (FLA 5000, FujiFilm). The band intensities representing ssDNA/ ssRNA and dsDNA/dsRNA were quantitated using the ImageQuant software (Pharmacia). The fraction of unwound DNA or RNA was plotted against the concentration of the compound (Log) and the $EC_{50}$ was determined by non-linear regression using the GraphPad Prism (GraphPad Inc). Experiments were repeated at least three times.

I. ATP Hydrolysis Assay

ATP hydrolysis measurements were carried out under conditions similar to those used in the gel-based unwinding assays. 50 nM nsp13 was pre-incubated with varying concentrations of the compound (0 µM, 2.5 µM, 5 µM, 10 µM, 20 µM and 40 µM). Reactions were performed in a buffer consisting of 20 mM HEPES pH 7.5, 20 mM NaCl, 5 mM $MgCl_2$, 1 mM DTT, 0.1 mg/ml BSA, and 5% glycerol and initiated with 5 µM $\gamma^{-32}P$-ATP. Samples were rapidly mixed at 30° C. and reactions were allowed to proceed for 10 seconds prior to quenching with 100 mM EDTA, 0.2% SDS, and 20% glycerol. Reaction products were separated by thin-layer chromatography on polyethyleneimine-cellulose F plates (Merck) using 0.5 M lithium chloride as the liquid phase and visualized by autoradiography. The fraction of hydrolyzed monophosphate (Pi) was quantitated using the ImageQuant software (Pharmacia). Experiments were repeated at least three times.

J. DNA-Binding Assay

To determine if the selected compound affects the binding affinity of nsp13 for nucleic acid, gel mobility shift assays were performed. The binding of 60/40-mer (20ss:40ds) DNA substrates (FIG. 10) was measured at various concentrations of the inhibitor in a reaction mixture containing 25 nM nsp13, 20 mM Hepes, pH 7.5, 20 mM NaCl, 5 mM $MgCl_2$, 1 mM DTT, 0.1 mg/ml BSA and 5% glycerol at 30° C. for 20 minutes. The concentration of 5'-Cy3-labeled dsDNA was 5 nM. Samples were electrophoresed at 100 V for 1.5 h at 4° C. on a 6% non-denaturing polyacrylamide gel, using 89 mM Tris-Borate, pH 8.2. Gels were scanned in a PhosphorImager and quantitated by ImageQuant (Amersham Biosciences).

K. Enzyme Kinetics

To determine the inhibition mode with respect to ATP (competitive or non-competitive), the 96-well fluorescence-based assay was used to measure the effect of SSYA10-001 in the helicase activity of nsp13. 25 µl reactions containing 50 nM nsp13, 20 mM Hepes, pH 7.5, 20 mM NaCl, 5 mM $MgCl_2$ and varying SSYA 10-001 (0-20 µM) were initiated by adding 100 nM fluorescein and black hole quencher-dsDNA. These reactions also included increasing amounts of ATP (0.0125 mM-7.5 mM). For determining the inhibition mode with respect to nucleic acid, the fluorescein and black hole quencher-labeled substrate concentrations were varied (0.01-1 µM) in the presence of 2 mM ATP and increasing amounts of SSYA10-001 (from 0-20 µM). The reactions were allowed to proceed for 10 minutes at 30° C. and fluorescence was measured. Assays were carried out in three independent experiments. Results were analyzed in Lineweaver-Burk graphs (1/V vs. 1/[S] for various [SSYA10-001] and Dixon plots (1/V vs. [SSYA10-001]) were used to determine the inhibitor $K_i$ from the X-axis intercept (See Sarafianos, S. G., U. Kortz, M. T. Pope, and M. J. Modak. 1996. Mechanism of polyoxometalate-mediated inactivation of DNA polymerases: an analysis with HIV-1 reverse transcriptase indicates specificity for the DNA-binding cleft. Biochem J 319 (Pt 2):619-626) (GraphPad Prism 5.0, GraphPad Inc).

L. Primer Extension and Strand Displacement Assay with Klenow Fragment

DNA template was annealed to a 5'-Cy3-labeled DNA primer and a third oligonucleotide corresponding to the first 14 nucleotides of the DNA template at the 5' end (FIG. 7, FIG. 10). To monitor the primer extension, 10 nM DNA substrate (14ds:4ss:18ds DNA substrate, FIG. 10) was incubated with varying concentrations of SSYA10-001 (0, 5, 10 and 20 µM) or pico green reagent (Invitrogen) (0×, 1×, 2×, 3× as directed by the manufacturer) in a buffer containing 50 mM Tris pH 7.5, and 50 mM NaCl, 5 mM $MgCl_2$, 1 mM DTT, and 5% glycerol. The reactions were initiated by the addition of 20 nM KF to a final volume of 20 µl. All dNTPs were present at a final concentration of 50 µM. The reactions were terminated after 15 min by adding an equal volume of 100% formamide containing traces of bromophenol blue. The products were resolved on a 15% polyacrylamide 7 M urea gel. In this and subsequent assays, the gels were scanned with a phosphorimaging device (FLA 5000, FujiFilm).

M. Pico Green Assay

To measure pico green activity, 1× final concentration of pico green reagent was incubated with 50 nM dsDNA (31/18-mer) in a buffer containing 10 mM Tris-HCl, 1 mM EDTA, pH 7.5 in total volume of 200 µl in 96-well microplates, and fluorescence was measured ~2 mins after incubation using a CytoFluor microplate reader. Samples were excited at 485 nm and fluorescence intensity was measured at 520 nm. To determine if the SSYA10-001 binds nucleic acid, varying concentrations of the compound (0, 2.5, 5, 10, 20 and 40 µM) was preincubated with 50 nM dsDNA (31/18-mer) for 10 mins followed by addition of 1× final concentration of pico green reagent, and immediate fluorescence measurement.

N. SARS-CoV Replicon Assay with RNA Detection by Reverse Transcription and Quantitative Real-Time PCR The SARS-CoV replicon was prepared as described previously (See Almazan, F., M. L. Dediego, C. Galan, D. Escors, E. Alvarez, J. Ortego, I. Sola, S. Zuniga, S. Alonso, J. L. Moreno, A. Nogales, C. Capiscol, and L. Enjuanes. 2006. Construction of a severe acute respiratory syndrome coronavirus infectious cDNA clone and a replicon to study coronavirus RNA synthesis. J Virol 80:10900-10906.). The Rep1b deletion mutant (most of the rep1b region has been deleted) was generated by digesting and ligating the SA RS replicon with Bsu36I at regions 16562/16565 and 29013/29016 of the SARS-CoV replicon. 293T cells were grown to 95% confluence on 35-mm-diameter plates and transfected with 4 µg of SARS-CoV Replicon, SARS-CoV non-replicative construct (NRC) (Rep1b deletion mutant) or mock plasmid by using Lipofectamine reagent (Invitrogen) as directed by the manufacturer. Varying concentrations of SSYA 10-001 (0, 2.5, 5, 10, and 20 µM) were added to the replicon-transfected cells and NRC-transfected cells. Total intracellular RNA was extracted at 48 hours post transfection (hpt) using the Trizol reagent (Invitrogen) followed by DNase I treatment to digest any remnant DNA. The extracted RNA was used as a template for Reverse Transcription and Quantitative real-time PCR (RT-qPCR) analysis of N gene mRNA synthesis (NC). The reverse primer URB-28630RS (5'-TGCTTCCCTCTGCG-TAGAAGCC-3') (SEQ ID NO: 22), complementary to nucleotides 511 to 532 of the N gene, and the forward primer URB-29VS (5'-GCCAACCAACCTCGATCTCTTG-3') (SEQ ID NO: 23), spanning nucleotides 29 to 50 of the Urbani leader sequence were used for amplification using the SuperScript® One-Step RT-qPCR System with Platinum®Taq DNA Polymerase (Invitrogen) by adhering to the manufacturer's specifications. This system is a real-time quantitative PCR that utilizes Sybr green for the detection and quantitation of the amplified DNA. The sequences for the forward and reverse primers for the amplification of U6 mRNA as endogenous control were as follows: 5'CTCGCT-TCGGCAGCACA-3' (SEQ ID NO: 24) for the U6 forward primer; 5'-AACGCTTCACGAATTTGCGT-3' (SEQ ID NO:

25) for the U6 reverse primer. Primer pair amplification efficiencies were determined using 1:10 cDNA dilutions; the test and housekeeping gene primer pairs with similar efficiencies were used for the qPCR reactions. Samples were normalized internally using the cycle threshold (CT) of the housekeeping gene, U6, as follows: $\Delta CT = (CT\ NC) - (CT\ U6)$. This is followed by determination of the mean of each sample, since the reactions were performed in triplicate. The mean value of each sample was normalized to the mean value of the NRC-cells using the following equation: $\Delta\Delta CT = \Delta CT(Sample) - \Delta CT(NRC)$. The Relative quantity (RQ) values were calculated as follows: $RQ = (2^{-\Delta\Delta CT})$. The RQ value for each sample was then normalized to the RQ value of the NRC (which is 1), in order to obtain percent relative RQ values. The data were graphed as percent relative replicon activity against the log of the inhibitor concentrations in μM using the dose response curve in GraphPad prism 5.0 (GraphPad Inc). Data presented represent experiments performed in triplicate from 3 independent experiments.

O. Assessment of Cytotoxicity

The effect of the inhibitors on cellular viability was assessed using a commercially available kit (Roche Diagnostics, Indianapolis, Ind.) that measures metabolism of XTT 2,3-bis(2-methoxy-4-nitro-5-sulfophenyl)-5-[(phenylamino) carbonyl]-2H-tetrazolium hydroxide). XTT is a tetrazolium salt that is converted by mitochondrial succinate dehydrogenase to a soluble orange-colored formazan product, which retains activity only in metabolically active cells. The amount of product is proportional to the number of living cells and can be spectrophotometrically quantified. The assay was performed in triplicates as described previously (Durk, R. C., K. Singh, C. A. Cornelison, D. K. Rai, K. B. Matzek, M. D. Leslie, E. Schafer, B. Marchand, A. Adedeji, E. Michailidis, C. A. Dorst, J. Moran, C. Pautler, L. L. Rodriguez, M. A. McIntosh, E. Rieder, and S. G. Sarafianos. 2010. Inhibitors of foot and mouth disease virus targeting a novel pocket of the RNA-dependent RNA polymerase. PLoS One 5:e15049.). Briefly, human embryonic kidney (HEK-293T) cells were seeded to 90% confluency in a 96-well plate. Cells were incubated for 48 hours with varying concentrations of the inhibitor (50 nM-250 μM) in a final volume of 100 μL DMEM media with 10% FBS and 50 μg/mL of penicillin G and streptomycin. Cells treated with Triton X-100 were used as a control for loss of cell viability. After the 48-hour incubation period the medium was removed and replaced with phenol red-free media. 20 μL of XTT was added per well and cells were incubated for an additional 3.5 hours. After incubation, the optical density at 450 nm was read by a plate reader and the $CC_{50}$ was determined by plotting the percent relative cell viability against inhibitor concentration using the sigmoidal dose response curve in Graphpad Prism 5.0 (GraphPad Inc.).

The invention claimed is:
1. A pharmaceutical composition comprising a compound of formula I:

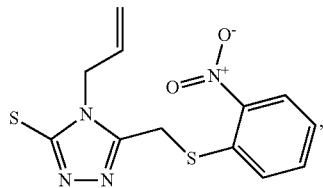 [SMILES: C=CCn1c(S)nnc1CSc1ccccc1[N+](=O)[O-]]

or a pharmaceutically acceptable salt thereof; and one or more pharmaceutically acceptable excipients or carriers, wherein the excipient or carrier is selected from the group consisting of an ion exchanger, alumina, aluminum stearate, lecithin, a serum protein, human serum albumin, phosphate, glycine, sorbic acid, potassium sorbate, vegetable fatty acids, protamine sulfate, disodium hydrogen phosphate, potassium hydrogen phosphate, a zinc salt, colloidal silica, magnesium trisilicate, polyvinyl pyrrolidone, cellulose, polyethylene glycol, sodium carboxymethylcellulose, polyacrylates, wax, polyethylene-polyoxypropylene-block polymer, polyethylene glycol, wool fat, lactose, dried corn starch, Ringer's solution, dextrose, Hank's solution, ethyl oleate, isopropyl myristate, sucrose, sorbitol, mannitol, gum acacia, calcium phosphate, mineral oil, cocoa butter, oil of theobroma, alginates, tragacanth, gelatin, methylcellulose, polyoxyethylene, sorbitan monolaurate, methyl hydroxybenzoate, propyl hydroxybenzoate, talc and magnesium stearate, alcohol, mineral oil, petrolatum, propylene glycol, polyoxyethylene, and polyoxypropylene.

2. A method for treating a subject suspected of needing treatment for a Nidovirales virus infection, comprising: administering to the subject an effective amount of a pharmaceutical composition comprising a compound of formula I:

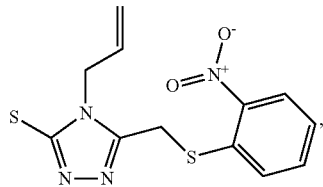 [SMILES: C=CCn1c(S)nnc1CSc1ccccc1[N+](=O)[O-]]

or a pharmaceutically acceptable salt thereof; and one or more pharmaceutically acceptable excipients.

3. The method of claim 2, wherein the Nidovirales virus infection is Severe Acute Respiratory Syndrome (SARS).

4. The method of claim 2, wherein the Nidovirales virus comprises a SARS-associated coronavirus (SARS-CoV).

5. The method of claim 2, wherein the Nidovirales virus comprises a Coronaviridae virus.

6. The method of claim 2, wherein the Nidovirales virus comprises a Middle East respiratory syndrome coronavirus (MERS-CoV).

7. The method of claim 2, wherein the Nidovirales virus comprises human coronavirus 299E (HCoV-229E) and/or human coronavirus NL63 (HCoV-NL63).

8. The method of claim 2, comprising administering the pharmaceutical composition by an oral route of administration.

9. The method of claim 2, comprising administering the pharmaceutical composition by a non-oral route of administration.

10. The method of claim 2, wherein administering is selected from the group consisting of administering parenterally, intravenously, subcutaneously, and intraperitoneally.

11. The method of claim 2, wherein administering is selected from the group consisting of administering transdermally, sublingually, and buccally.

12. The method of claim 2, wherein the subject is a mammal.

13. The method of claim 2, wherein the subject is an animal.

14. The method of claim 2, wherein the subject is a human.

15. The method of claim 2, further comprising identifying the subject as needing treatment for a Nidovirales virus infection.

16. The method of claim 2, wherein the subject suspected of needing treatment is suspected of having been exposed to a Nidovirales virus infection.

17. A method of inhibiting replication of a Nidovirales virus comprising the step of contacting a sample containing the Nidovirales virus with a compound of formula I:

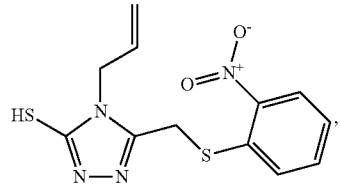 [SMILES: C=CCn1c(S)nnc1CSc1ccccc1[N+](=O)[O-]]

or a salt thereof.

* * * * *

SEQUENCE LISTING

```
<160> NUMBER OF SEQ ID NOS: 16

<210> SEQ ID NO 1
<211> LENGTH: 28
<212> TYPE: DNA
<213> ORGANISM: Artificial sequence
<220> FEATURE:
<223> OTHER INFORMATION: Synthesized oligonucleotides

<400> SEQUENCE: 1
tcaccaccac gtatctgagc ctgggcga                                              28

<210> SEQ ID NO 2
<211> LENGTH: 28
<212> TYPE: DNA
<213> ORGANISM: Artificial sequence
<220> FEATURE:
<223> OTHER INFORMATION: Synthesized oligonucleotides

<400> SEQUENCE: 2
tcgcccaggc tcagatacga ccaccact                                              28

<210> SEQ ID NO 3
<211> LENGTH: 28
<212> TYPE: DNA
<213> ORGANISM: Artificial sequence
<220> FEATURE:
<223> OTHER INFORMATION: Synthesized oligonucleotides

<400> SEQUENCE: 3
tcaccaccac gtatctgagc ctgggcga                                              28

<210> SEQ ID NO 4
<211> LENGTH: 28
<212> TYPE: DNA
<213> ORGANISM: Artificial sequence
<220> FEATURE:
<223> OTHER INFORMATION: Synthesized oligonucleotides
```

<400> SEQUENCE: 4
tcgcccaggc tcagatacga ccaccact                              28

<210> SEQ ID NO 5
<211> LENGTH: 28
<212> TYPE: DNA
<213> ORGANISM: Artificial sequence
<220> FEATURE:
<223> OTHER INFORMATION: Synthesized oligonucleotides

<400> SEQUENCE: 5
tcaccaccac gtatctgagc ctgggcga                              28

<210> SEQ ID NO 6
<211> LENGTH: 28
<212> TYPE: RNA
<213> ORGANISM: Artificial sequence
<220> FEATURE:
<223> OTHER INFORMATION: Synthesized oligonucleotides

<400> SEQUENCE: 6
ucgcccaggc ucagauacga ccaccacu                              28

<210> SEQ ID NO 7
<211> LENGTH: 31
<212> TYPE: DNA
<213> ORGANISM: Artificial sequence
<220> FEATURE:
<223> OTHER INFORMATION: Synthesized oligonucleotides

<400> SEQUENCE: 7
cgcagtcttc tcctggtgct cgaacagtga c                          31

<210> SEQ ID NO 8
<211> LENGTH: 18
<212> TYPE: DNA
<213> ORGANISM: Artificial sequence
<220> FEATURE:
<223> OTHER INFORMATION: Synthesized oligonucleotides

<400> SEQUENCE: 8
gtcactgttc gagcacca                                         18

<210> SEQ ID NO 9
<211> LENGTH: 31
<212> TYPE: RNA
<213> ORGANISM: Artificial sequence
<220> FEATURE:
<223> OTHER INFORMATION: Synthesized oligonucleotides

<400> SEQUENCE: 9
cgcagucuuc uccuggugcu cgaacaguga c                          31

<210> SEQ ID NO 10
<211> LENGTH: 18
<212> TYPE: RNA
<213> ORGANISM: Artificial sequence
<220> FEATURE:
<223> OTHER INFORMATION: Synthesized oligonucleotides

<400> SEQUENCE: 10
gucacuguuc gagcacca                                         18

<210> SEQ ID NO 11
<211> LENGTH: 44

```
<212> TYPE: DNA
<213> ORGANISM: Artificial sequence
<220> FEATURE:
<223> OTHER INFORMATION: Synthesized oligonucleotides

<400> SEQUENCE: 11
gatagccata gagccctaga tagcattggt gctcgaacag tgac                    44

<210> SEQ ID NO 12
<211> LENGTH: 40
<212> TYPE: DNA
<213> ORGANISM: Artificial sequence
<220> FEATURE:
<223> OTHER INFORMATION: Synthesized oligonucleotides

<400> SEQUENCE: 12
gtcactgttc gagcaccaat gctatcgctc tatggctatc                        40

<210> SEQ ID NO 13
<211> LENGTH: 31
<212> TYPE: RNA
<213> ORGANISM: Artificial sequence
<220> FEATURE:
<223> OTHER INFORMATION: Synthesized oligonucleotides

<400> SEQUENCE: 13
gcacuguaaa ugcauugcca gaaacaacug c                                 31

<210> SEQ ID NO 14
<211> LENGTH: 18
<212> TYPE: RNA
<213> ORGANISM: Artificial sequence
<220> FEATURE:
<223> OTHER INFORMATION: Synthesized oligonucleotides

<400> SEQUENCE: 14
gcaguuguuu cuggcaau                                                18

<210> SEQ ID NO 15
<211> LENGTH: 60
<212> TYPE: DNA
<213> ORGANISM: Artificial sequence
<220> FEATURE:
<223> OTHER INFORMATION: Synthesized oligonucleotides

<400> SEQUENCE: 15
tagatagcat tagatagcca cagatagcat cctagatagc attggtgctc gaacagtgac   60

<210> SEQ ID NO 16
<211> LENGTH: 40
<212> TYPE: DNA
<213> ORGANISM: Artificial sequence
<220> FEATURE:
<223> OTHER INFORMATION: Synthesized oligonucleotides

<400> SEQUENCE: 16
gtcactgttc gagcaccaat gctatctagg atgctatctg                        40
```